(12) United States Patent
DeHennis

(10) Patent No.: US 11,116,402 B2
(45) Date of Patent: Sep. 14, 2021

(54) CONTINUOUS ANALYTE MONITORING SYSTEM

(71) Applicant: Senseonics, Incorporated, Germantown, MD (US)

(72) Inventor: Andrew DeHennis, Germantown, MD (US)

(73) Assignee: Senseonics, Incorporated, Germantown, MD (US)

(*) Notice: Subject to any disclaimer, the term of this patent is extended or adjusted under 35 U.S.C. 154(b) by 238 days.

(21) Appl. No.: 16/116,556

(22) Filed: Aug. 29, 2018

(65) Prior Publication Data

US 2018/0368685 A1   Dec. 27, 2018

Related U.S. Application Data

(60) Continuation of application No. 15/810,822, filed on Nov. 13, 2017, which is a division of application No.
(Continued)

(51) Int. Cl.
*A61B 5/1455* (2006.01)
*A61B 5/00* (2006.01)
(Continued)

(52) U.S. Cl.
CPC .......... *A61B 5/0022* (2013.01); *A61B 5/002* (2013.01); *A61B 5/1459* (2013.01);
(Continued)

(58) Field of Classification Search
None
See application file for complete search history.

(56) References Cited

U.S. PATENT DOCUMENTS 5,846,188 A    12/1998  Palti
6,304,766 B1 * 10/2001  Colvin, Jr. .......... A61B 5/0031
                                                128/903
(Continued)

FOREIGN PATENT DOCUMENTS

EP    1030590 B1   10/2002
EP    2270481 B1    5/2014
(Continued)

*Primary Examiner* — Eric F Winakur
*Assistant Examiner* — Marjan Fardanesh
(74) *Attorney, Agent, or Firm* — Rothwell, Figg, Ernst & Manbeck, P.C.

(57) ABSTRACT

An improved analyte monitoring system having a sensor and a transceiver with improved communication and/or user interface capabilities. The transceiver may communicate with and power the sensor. The transceiver may receive one or more analyte measurements from the sensor and may calculate one or more analyte concentrations based on the received analyte measurements. The transceiver may generate analyte concentration trends, alerts, and/or alarms based on the calculated analyte concentrations. The system may also include a display device, which may be, for example, a smartphone and may be used to display analyte measurements received from the transceiver. The display device may execute a mobile medical application. The system may include a data management system, which may be web-based.

13 Claims, 16 Drawing Sheets

Related U.S. Application Data

14/580,289, filed on Dec. 23, 2014, now Pat. No. 9,814,389.

(60) Provisional application No. 61/922,387, filed on Dec. 31, 2013.

(51) Int. Cl.
*A61B 5/145* (2006.01)
*A61B 5/1459* (2006.01)
*G16H 40/63* (2018.01)
*G06F 19/00* (2018.01)

(52) U.S. Cl.
CPC ............ *A61B 5/14532* (2013.01); *A61B 5/74* (2013.01); *A61B 5/7455* (2013.01); *G06F 19/00* (2013.01); *G16H 40/63* (2018.01); *A61B 5/7275* (2013.01); *A61B 2560/0209* (2013.01); *A61B 2560/0219* (2013.01)

(56) References Cited

U.S. PATENT DOCUMENTS

| | | |
|---|---|---|
| 6,330,464 B1 | 12/2001 | Colvin, Jr. et al. |
| 6,477,424 B1 | 11/2002 | Thompson et al. |
| 6,577,899 B2 | 6/2003 | Lebel et al. |
| 6,635,167 B1 | 10/2003 | Batman et al. |
| 7,022,072 B2 | 4/2006 | Fox et al. |
| 7,034,677 B2 | 4/2006 | Steinthal et al. |
| 7,401,111 B1 | 7/2008 | Batman et al. |
| 8,073,548 B2 | 12/2011 | Colvin, Jr. et al. |
| 8,579,815 B2 | 11/2013 | Galley et al. |
| 8,922,366 B1 | 12/2014 | Honore et al. |
| 9,226,714 B2 | 1/2016 | Harper et al. |
| 9,262,586 B2 | 2/2016 | Steiger et al. |
| 9,414,775 B2 | 8/2016 | Colvin, Jr. et al. |
| 9,498,165 B2 | 11/2016 | Johnson et al. |
| 9,504,430 B2 | 11/2016 | Johnson et al. |
| 9,693,714 B2 | 7/2017 | DeHennis et al. |
| 9,907,470 B2 | 3/2018 | Goodnow et al. |
| 9,947,201 B2 | 4/2018 | Johnson et al. |
| 9,949,642 B2 | 4/2018 | Love et al. |
| 10,022,499 B2 | 7/2018 | Galasso |
| 10,052,049 B2 | 8/2018 | Blomquist et al. |
| 10,123,752 B2 | 11/2018 | Harper et al. |
| 10,177,609 B2 | 1/2019 | Olson et al. |
| 2002/0016534 A1* | 2/2002 | Trepagnier ......... A61B 5/14532 600/316 |
| 2002/0151772 A1 | 10/2002 | Polak |
| 2006/0047327 A1 | 3/2006 | Colvin et al. |
| 2008/0129486 A1 | 6/2008 | Jeckelmann et al. |
| 2009/0036760 A1 | 2/2009 | Hayter |
| 2009/0135003 A1* | 5/2009 | Charlier ............... G01J 1/0266 340/539.13 |
| 2010/0261987 A1 | 10/2010 | Kamath et al. |
| 2012/0130203 A1 | 5/2012 | Stergiou et al. |
| 2012/0226117 A1* | 9/2012 | Lamego ............... A61B 5/7475 600/316 |
| 2012/0245447 A1 | 9/2012 | Karan et al. |
| 2013/0006069 A1 | 1/2013 | Gil et al. |
| 2013/0211213 A1 | 8/2013 | DeHennis et al. |
| 2013/0241745 A1* | 9/2013 | Colvin, Jr. ............. A61B 5/076 340/870.02 |
| 2013/0331667 A1 | 12/2013 | Colvin, Jr. et al. |
| 2014/0012117 A1 | 1/2014 | Mensinger et al. |
| 2014/0012118 A1 | 1/2014 | Mensinger et al. |
| 2014/0012510 A1* | 1/2014 | Mensinger ............. A61B 5/742 702/19 |
| 2014/0081100 A1* | 3/2014 | Muhsin ................. A61B 5/742 600/324 |
| 2014/0118104 A1 | 5/2014 | Sicurello et al. |
| 2016/0270740 A1 | 9/2016 | Raisoni et al. |
| 2018/0125364 A1 | 5/2018 | DeHennis |

FOREIGN PATENT DOCUMENTS

| | | |
|---|---|---|
| EP | 3 078 013 A1 | 10/2016 |
| WO | 2011/133768 A1 | 10/2011 |
| WO | 2015/084947 A1 | 6/2015 |

* cited by examiner

Reader Log

Drag a column header here to group by that column

| Event Date | Event Time | Event Name | Value | UOM | Comments | Other Info |
|---|---|---|---|---|---|---|
| 01/20/2012 | 00:00:00 | Glucose Reading | 360 | mg/dL | | |
| 01/20/2012 | 00:02:00 | Glucose Reading | 359 | mg/dL | | |
| 01/20/2012 | 00:04:00 | Glucose Reading | 362 | mg/dL | | |
| 01/20/2012 | 00:06:00 | Glucose Reading | 362 | mg/dL | | |
| 01/20/2012 | 00:08:00 | Glucose Reading | 364 | mg/dL | | |
| 01/20/2012 | 00:10:00 | Glucose Reading | 359 | mg/dL | | |
| 01/20/2012 | 00:12:00 | Glucose Reading | 354 | mg/dL | | |
| 01/20/2012 | 00:14:00 | Glucose Reading | 352 | mg/dL | | |
| 01/20/2012 | 00:16:00 | Glucose Reading | 349 | mg/dL | | |
| 01/20/2012 | 00:18:00 | Glucose Reading | 346 | mg/dL | | |
| 01/20/2012 | 00:20:00 | Glucose Reading | 343 | mg/dL | | |
| 01/20/2012 | 00:22:00 | Glucose Reading | 342 | mg/dL | | |
| 01/20/2012 | 00:24:00 | Glucose Reading | 344 | mg/dL | | |
| 01/20/2012 | 00:26:00 | Glucose Reading | 348 | mg/dL | | |
| 01/20/2012 | 00:28:00 | Glucose Reading | 352 | mg/dL | | |
| 01/20/2012 | 00:30:00 | Glucose Reading | 354 | mg/dL | | |
| 01/20/2012 | 00:32:00 | Glucose Reading | 353 | mg/dL | | |
| 01/20/2012 | 00:34:00 | Glucose Reading | 351 | mg/dL | | |
| 01/20/2012 | 00:36:00 | Glucose Reading | 353 | mg/dL | | |
| 01/20/2012 | 00:38:00 | Glucose Reading | 348 | mg/dL | | |

Page 1 of 253 (5046 items)  ⊙ 1 2 3 4 5 6 7 ... 251 252 253 ⊙

▽ Create Filter

FIG. 14

CONTINUOUS ANALYTE MONITORING SYSTEM

CROSS-REFERENCE TO RELATED APPLICATIONS

The present application is a continuation of U.S. patent application Ser. No. 15/810,822, filed Nov. 13, 2017, which is a divisional of U.S. patent application Ser. No. 14/580,289, filed on Dec. 23, 2014, now U.S. Pat. No. 9,814,389, which claims the benefit of priority to U.S. Provisional Application No. 61/922,387, filed on Dec. 31, 2013, which are incorporated herein by reference in their entireties.

BACKGROUND

Field of Invention

The present invention relates generally to measurement of an analyte in a medium of a living animal using a system including a sensor and a transceiver. Specifically, the present invention may relate to a continuous analyte monitoring system having communication and/or user interface capabilities.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels <7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence. There is presently a need in the art for an improved analyte monitoring systems.

SUMMARY

The present invention overcomes the disadvantages of prior systems by providing, among other advantages, an improved analyte monitoring system having improved communication and/or user interface capabilities.

One aspect of the invention may provide a system for detecting an amount or concentration of an analyte in vivo within a living organism. The system may include an analyte sensor, a transceiver configured to receive data signals from the analyte sensor and convey analyte information, and a display device configured to receive analyte information and execute a mobile medical application that displays analyte concentrations.

Another aspect of the invention may provide a system for detecting an amount or concentration of an analyte in vivo within a living organism. The system may include an analyte sensor and an transceiver. In some embodiments, the transceiver can be external. In some embodiments, the receiver can be internal. The analyte sensor may include an analyte indicator, sensor elements, and a transceiver interface device. The analyte indicator may be configured to exhibit a detectable property based on the amount or concentration of the analyte in proximity to the analyte indicator. The sensor elements may be configured to generate a data signal based on the detectable property exhibited by the analyte indicator. The transceiver interface device may be configured to receive a power signal and generate power for powering the sensor elements and to convey data signals generated by the sensor elements. The transceiver may include a sensor interface device configured to convey the power signal to the transceiver interface device of the analyte sensor and to receive data signals conveyed by the transceiver interface device of the analyte sensor.

In some embodiments, the system may include a display device and/or a data management system. The external transceiver may comprise a processor configured to calculate analyte concentrations based on the received data signals. The transceiver may include a display interface device configured to convey the calculated analyte concentrations to the display device. The display device may be configured to receive the analyte concentrations conveyed by the display interface device of the transceiver and to display the received analyte concentrations. The display device may be configured to upload the received analyte concentrations to a web-based data management system. The display device may be a smartphone.

In some embodiments, the transceiver may comprise a display interface device configured to convey the received data signals to a display device. The system may include a display device configured to receive the data signals conveyed by the display interface device of the transceiver, to calculate analyte concentrations based on the received data signals, and to display the calculated analyte concentrations. The display device may be configured to calculate analyte concentration trends based on the calculated analyte concentrations and to generate alerts or alarms based on the calculated analyte concentrations.

In some embodiments, the analyte sensor may be a fully implantable sensor. The transceiver interface device of the analyte sensor may be an antenna configured to wirelessly receive the power signal from the external transceiver and to wirelessly convey the data signals generated by the sensor elements, and the sensor interface device of the transceiver may be an antenna configured to wirelessly convey the power signal to the antenna of the analyte sensor and to receive the data signals from the antenna of the analyte sensor. In other embodiments, the sensor interface device of the transceiver and the transceiver interface device of the analyte sensor may be a wire connected through a transdermal needle tip.

Another aspect of the invention may provide a transceiver including a sensor interface device and a display interface device. The sensor interface device may be configured to convey a power signal to an analyte sensor and to receive data signals conveyed by the analyte sensor. The display interface device may be configured to convey analyte information to a display device.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIG. 14 illustrates a transceiver log report generated by a data management system of an analyte monitoring system embodying aspects of the present invention.

DETAILED DESCRIPTION OF PREFERRED EMBODIMENTS

Figure 1A:
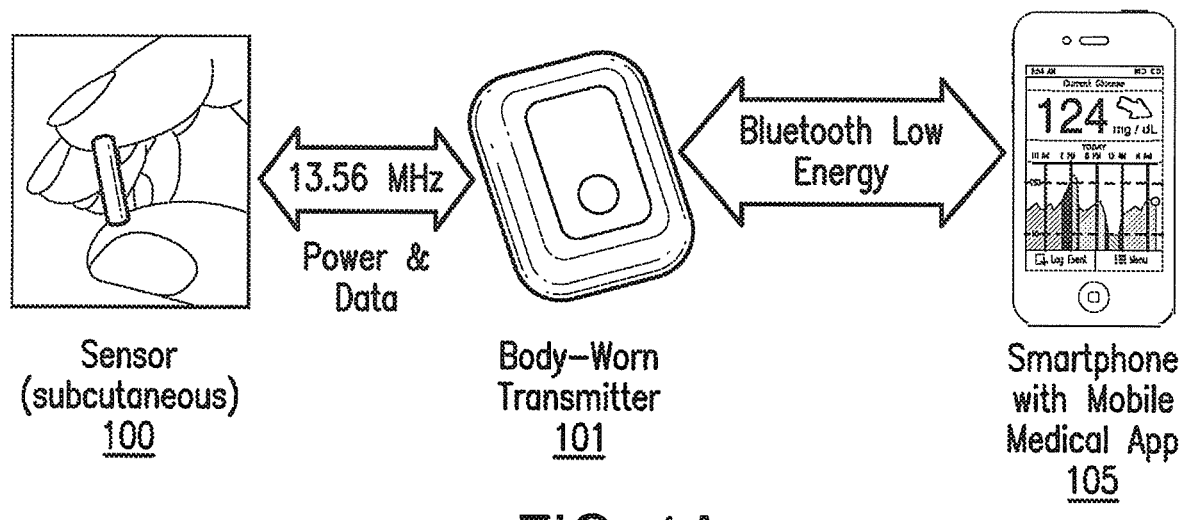
FIGS. 1A-1C are schematic views illustrating a sensor system embodying aspects of the present invention.
Figure 1B:
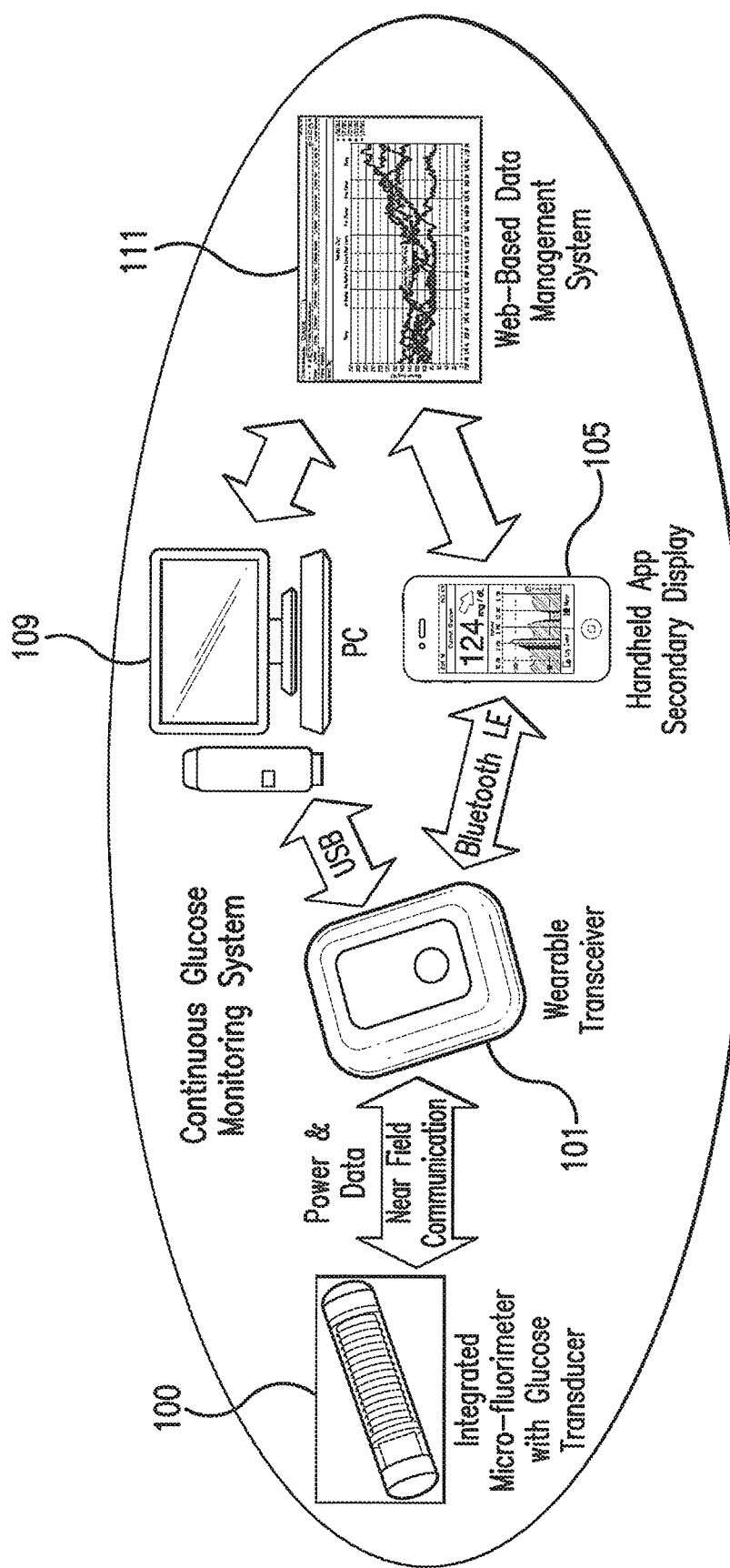
Figure 1C:
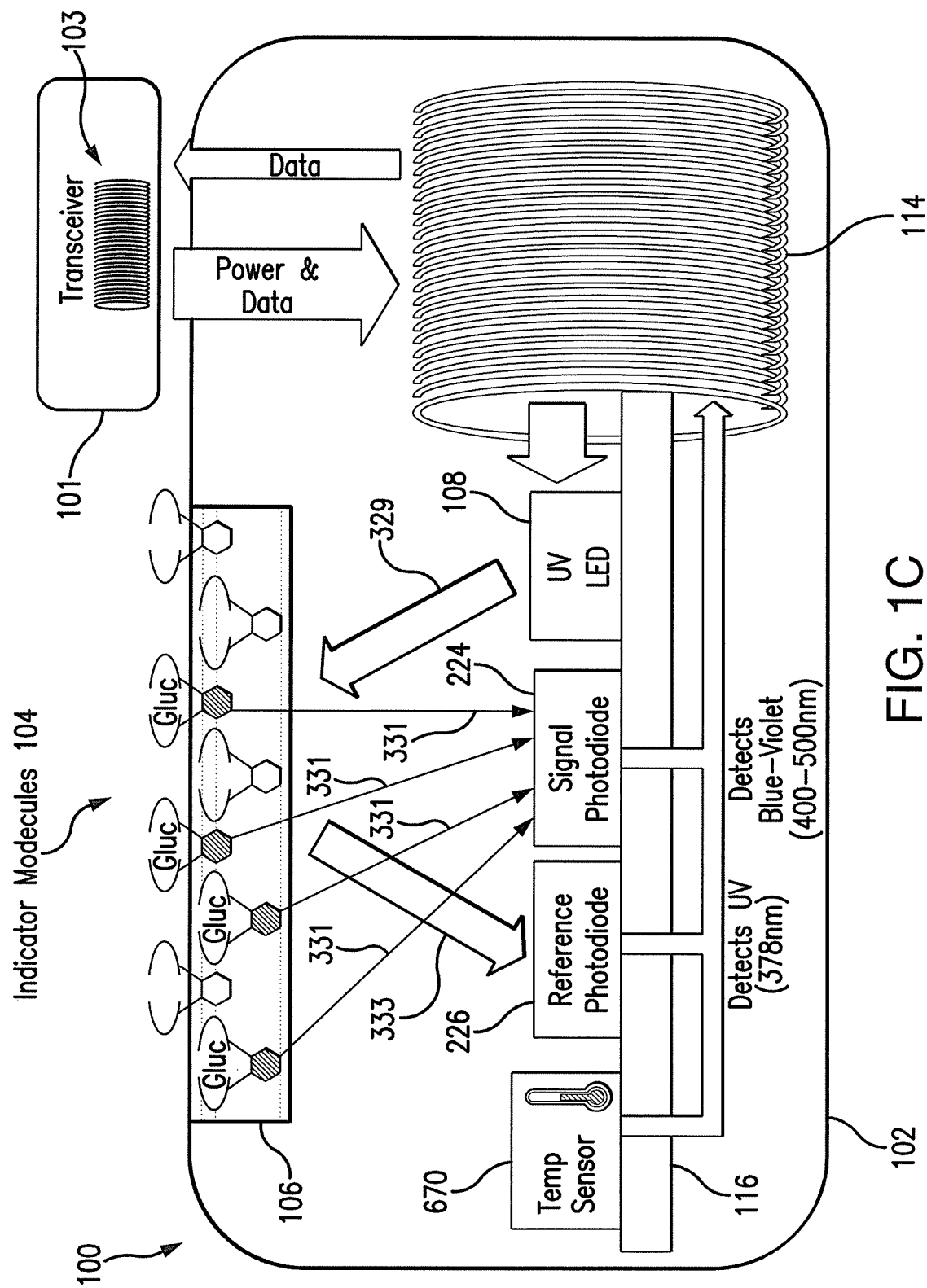

FIGS. 1A-1C are schematic views of an analyte monitoring system embodying aspects of the present invention. As illustrated in FIGS. 1A-1C, the system may include an analyte sensor 100 and an external transceiver 101. In some non-limiting embodiments, the sensor 100 may be a fully implantable continuous analyte (e.g., glucose, oxygen, cardiac markers, low-density lipoprotein (LDL), high-density lipoprotein (HDL), or triglycerides) monitoring sensor. The sensor 100 may be implanted in a living animal (e.g., a living human). The sensor 100 may be implanted, for example, in a living animal's arm, wrist, leg, abdomen, peritoneum, intravenously, or other region of the living animal suitable for sensor implantation. For example, in one non-limiting embodiment, the sensor 100 may be implanted beneath the skin (i.e., in the subcutaneous or peritoneal tissues). In some embodiments, the sensor 100 may be implanted subcutaneously (e.g., in a location of the body that is appropriate for subcutaneous measurement of interstitial fluid glucose), and no portion of the sensor 100 protrudes from the skin. In some embodiments, the sensor 100 may be an optical sensor (e.g., a fluorometer). In some embodiments, the sensor 100 may be a chemical or biochemical sensor. In some non-limiting embodiments, the sensor 100 may be capable of being continuously implanted for at least 90 days or longer and may replaced thereafter.

The transceiver 101 may be an electronic device that communicates with the sensor 100 to power the sensor 100 and/or receive measurement information (e.g., photodetector and/or temperature sensor readings) from the sensor 100. The measurement information may include one or more readings from one or more photodetectors of the sensor and/or one or more readings from one or more temperature sensors of the sensors. In some embodiments, the transceiver 101 may calculate analyte concentrations from the measurement information received from the sensor 100. However, it is not required that the transceiver 101 perform the analyte concentration calculations itself, and, in some alternative embodiments, the transceiver 101 may instead convey/relay the measurement information received from the sensor 100 to another device (e.g., display device 105) for calculation of analyte concentrations (e.g., by a mobile medical application executing on the display device 105).

In some embodiments, as illustrated in FIGS. 1A and 1B, the system may include a display device 105. In some embodiments, the display device 105 may be a portable and/or handheld device. As illustrated in FIGS. 1A and 1B, in some embodiments, the display device 105 may be a smartphone. However, this is not required, and, in alternative embodiments, the display device 105 may be a personal data assistant ("PDA"), a laptop computer, or a dedicated analyte monitoring display device. The display device 105 may have a mobile medical application installed thereon. In some embodiments, as illustrated in FIG. 1B, the system may include a personal computer (PC) 109. The transceiver 101 may communicate with the display device 105 and/or PC 109 through a wired or wireless connection. Moreover, in some embodiments, as illustrated in FIG. 1B, the display device 105 and/or PC 109 may communicate with a data management system (DMS) 111. In some embodiments, the DMS 111 may be a web-based DMS (e.g., hosted on a remote server). In some embodiments, the display device 105 may communicate with cloud storage.

In some embodiments, the analyte monitoring system may provide real-time readings, graphs, trends, and/or analyte alarms directly to a user (e.g., via a user interface of the transceiver 101 and/or display device 105). The system may be capable of being used in a home setting, and, in embodiments where the analyte is glucose, the system may aid people with diabetes mellitus in predicting and detecting episodes of hypoglycemia and hyperglycemia. The system may additionally or alternatively be capable of being used in clinical settings to aid health care professionals in evaluating analyte control. In some embodiments, the system may includes multiple sensors 100 (e.g., for redundancy).

In some embodiments (e.g., embodiments in which the sensor 100 is a fully implantable sensor), the transceiver 101 may implement a passive telemetry for communicating with the implantable sensor 100 via an inductive magnetic link for both power and data transfer. The sensor 100 may include an inductive element 114, which may be, for example, a ferrite based micro-antenna. In some embodiments, the inductive element 114 may be connected to analyte detection circuitry. For example, in some embodiments, where the sensor 100 is an optical sensor, the inductive element 114 may be connected to micro-fluorimeter circuitry (e.g., an application specification integrated circuit (ASIC)) and a related optical detection system of the sensor 100. In some embodiments, the sensor 100 may not include a battery, and, as a result, the sensor 100 may rely on the transceiver 101 to provide necessary power and a data link to convey analyte-related data back to transceiver 101.

In one non-limiting embodiment, the analyte monitoring system may continually record interstitial fluid glucose levels in people with diabetes mellitus for the purpose of improving diabetes management. The transceiver 101 may be wearable and may communicate with the sensor 100, which may be a passive, fully implantable sensor having a small size, such as, for example, the approximate size of a grain of rice. For a sensor 100 that is a fully implantable sensor having no battery power source, the transceiver 101 may provide energy to run the sensor 100 via a magnetic field. In some embodiments, the magnetic transceiver-sensor link can be considered as "weakly coupled transformer" type. The magnetic transceiver-sensor link may provide energy and a link for data transfer using amplitude modulation (AM). Although in some embodiments, data transfer is carried out using AM, in alternative embodiments, other types of modulation may be used. The magnetic transceiver-sensor link may have a low efficiency of power transfer and, therefore, may require relatively high power amplifier to energize the sensor 100 at longer distances. In some non-limiting embodiments, the analyte monitoring system may use a frequency of 13.56 MHz, which can achieve high penetration through the skin and is a medically approved frequency band, for power transfer. However, this is not required, and, in other embodiments, different frequencies may be used for powering and communicating with the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive (e.g., as part of a biocompatible patch), and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a reading from the sensor 100.

In some embodiments, as illustrated in FIG. 1C, the transceiver 101 may include an inductive element 103, such as, for example, a coil. The transceiver 101 may generate an electromagnetic wave or electrodynamic field (e.g., by using a coil) to induce a current in an inductive element 114 of the sensor 100, which powers the sensor 100. The transceiver 101 may also convey data (e.g., commands) to the sensor 100. For example, in a non-limiting embodiment, the transceiver 101 may convey data by modulating the electromagnetic wave used to power the sensor 100 (e.g., by modulating the current flowing through a coil 103 of the transceiver 101). The modulation in the electromagnetic wave generated by the transceiver 101 may be detected/extracted by the sensor 100. Moreover, the transceiver 101 may receive data (e.g., measurement information) from the sensor 100. For example, in a non-limiting embodiment, the transceiver 101 may receive data by detecting modulations in the electromagnetic wave generated by the sensor 100, e.g., by detecting modulations in the current flowing through the coil 103 of the transceiver 101.

The inductive element 103 of the transceiver 101 and the inductive element 114 of the sensor 100 may be in any configuration that permits adequate field strength to be achieved when the two inductive elements are brought within adequate physical proximity.

In some non-limiting embodiments, as illustrated in FIG. 1C, the sensor 100 may be encased in a sensor housing 102 (i.e., body, shell, capsule, or encasement), which may be rigid and biocompatible. The sensor 100 may include an analyte indicator element 106, such as, for example, a polymer graft coated, diffused, adhered, or embedded on or in at least a portion of the exterior surface of the sensor housing 102. The analyte indicator element 106 (e.g., polymer graft) of the sensor 100 may include indicator molecules 104 (e.g., fluorescent indicator molecules) exhibiting one or more detectable properties (e.g., optical properties) based on the amount or concentration of the analyte in proximity to the analyte indicator element. In some embodiments, the sensor 100 may include a light source 108 that emits excitation light 329 over a range of wavelengths that interact with the indicator molecules 104. The sensor 100 may also include one or more photodetectors 224, 226 (e.g., photodiodes, phototransistors, photoresistors, or other photosensitive elements). The one or more photodetectors (e.g., photodetector 224) may be sensitive to emission light 331 (e.g., fluorescent light) emitted by the indicator molecules 104 such that a signal generated by a photodetector (e.g., photodetector 224) in response thereto that is indicative of the level of emission light 331 of the indicator molecules and, thus, the amount of analyte of interest (e.g., glucose). In some non-limiting embodiments, one or more of the photodetectors (e.g., photodetector 226) may be sensitive to excitation light 329 that is reflected from the analyte indicator element 106 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the sensor 100 may include a temperature transducer 670. In some non-limiting embodiments, the sensor 100 may include a drug-eluting polymer matrix that disperses one or more therapeutic agents (e.g., an anti-inflammatory drug).

In some embodiments, as illustrated in FIG. 1C, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 116 with the remainder of the circuitry is secured to the semiconductor substrate 116, which may provide communication paths between the various secured components.

In some embodiments, the one or more of the sensor housing 102, analyte indicator element 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Although in some embodiments, as illustrated in FIGS. 1A-1C, the sensor 100 may be an optical sensor, this is not required, and, in one or more alternative embodiments, sensor 100 may be a different type of analyte sensor, such as, for example, a diffusion sensor or a pressure sensor. Also, although in some embodiments, as illustrated in FIGS. 1A-1C, the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of wirelessly communicating using inductive elements 103 and 114, the sensor 100 and transceiver 101 may communicate using one or more wires connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, the sensor 100 may include a transceiver interface device. In some embodiments where the sensor 100 includes an antenna (e.g., inductive element 114), the transceiver interface device may include the antenna (e.g., inductive element 114) of sensor 100. In some of the transcutaneous embodiments where there exists a wired connection between the sensor 100 and the transceiver 101, the transceiver interface device may include the wired connection.

Figure 2:
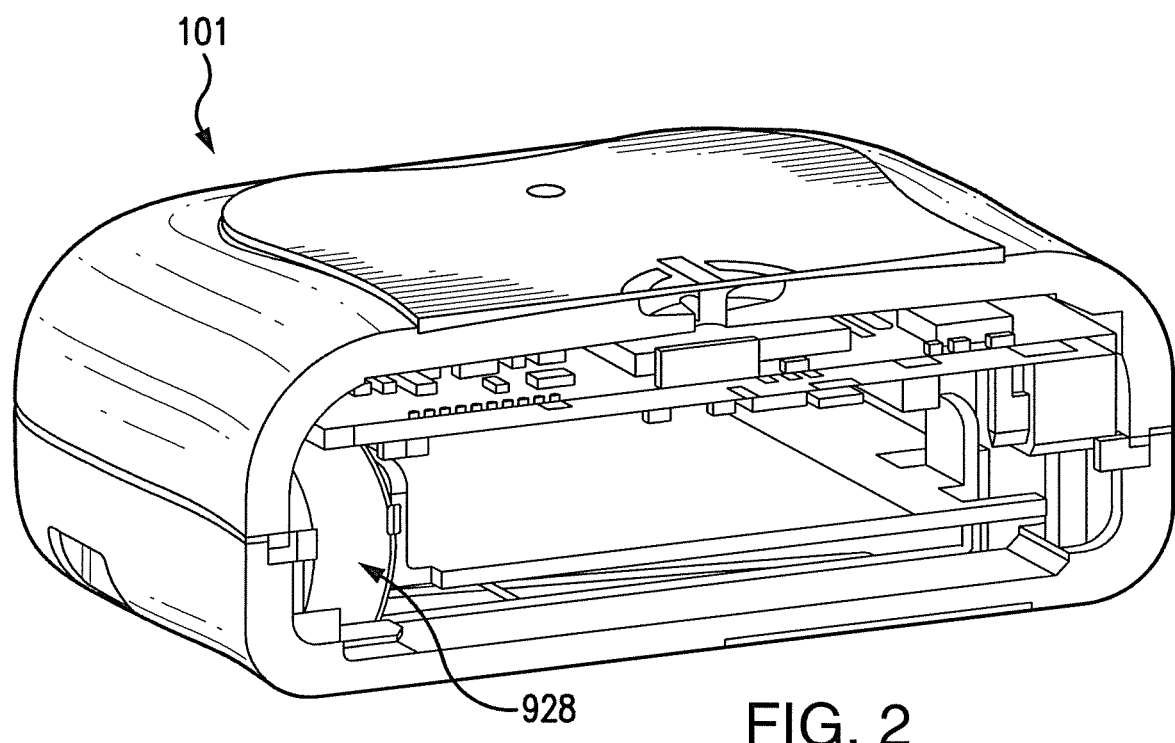
FIG. 2 is cross-sectional, perspective view of a transceiver embodying aspects of the invention.
Figure 3:
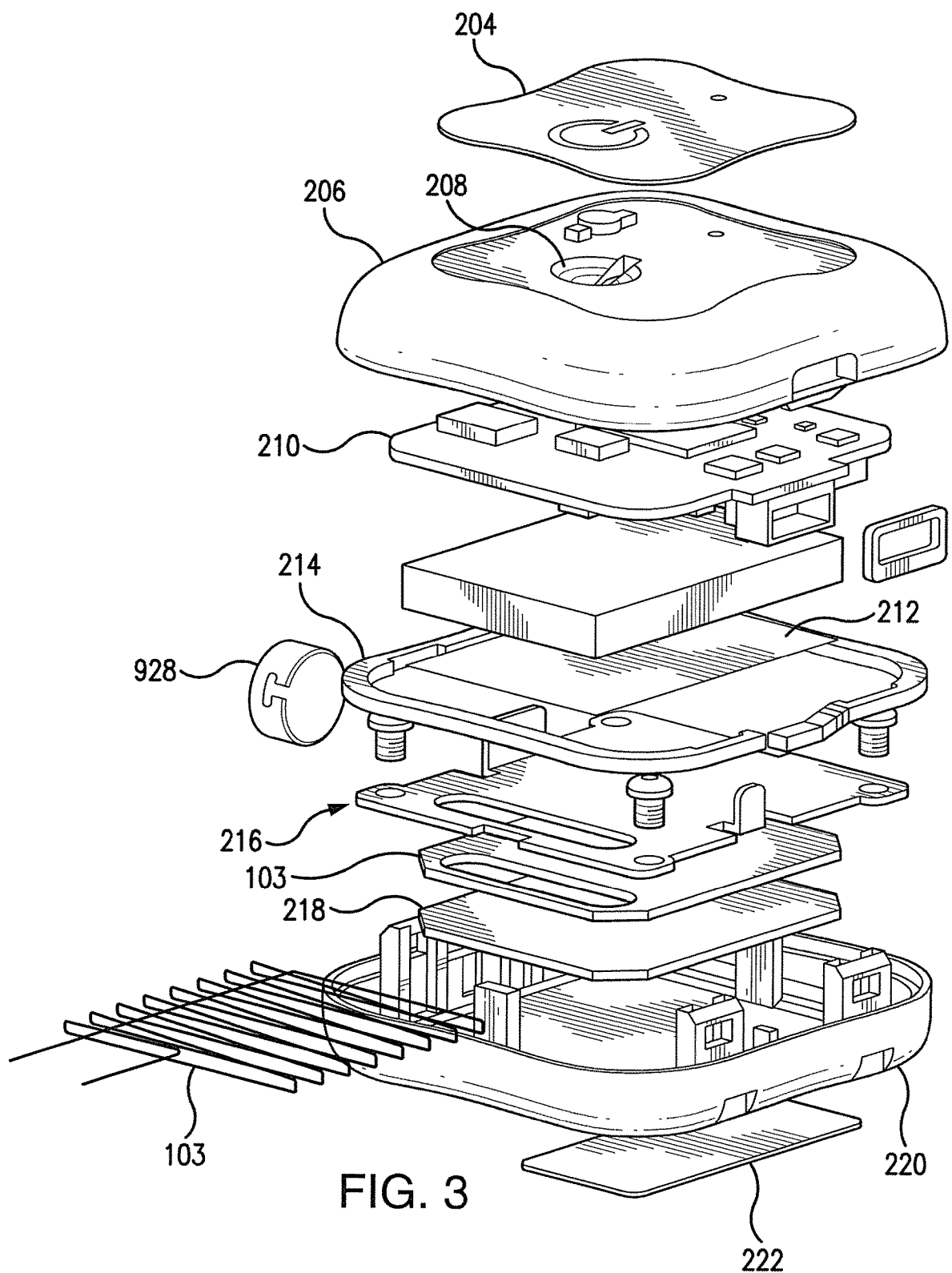
FIG. 3 is an exploded, perspective view of a transceiver embodying aspects of the invention.

FIGS. 2 and 3 are cross-sectional and exploded views, respectively, of a non-limiting embodiment of the transceiver 101, which may be included in the analyte monitoring system illustrated in FIGS. 1A-1C. As illustrated in FIG. 3, in some non-limiting embodiments, the transceiver 101 may include a graphic overlay 204, front housing 206, button 208, printed circuit board (PCB) assembly 210, battery 212, gaskets 214, antenna 103, frame 218, reflection plate 216, back housing 220, ID label 222, and/or vibration motor 928. In some non-limiting embodiments, the vibration motor 928 may be attached to the front housing 206 or back housing 220 such that the battery 212 does not dampen the vibration of vibration motor 928. In a non-limiting embodiment, the transceiver electronics may be assembled using standard surface mount device (SMD) reflow and solder techniques.

In one embodiment, the electronics and peripherals may be put into a snap together housing design in which the front housing 206 and back housing 220 may be snapped together. In some embodiments, the full assembly process may be performed at a single external electronics house. However, this is not required, and, in alternative embodiments, the transceiver assembly process may be performed at one or more electronics houses, which may be internal, external, or a combination thereof. In some embodiments, the assembled transceiver may be programmed and functionally tested. In some embodiments, assembled transceivers 101 may be packaged into their final shipping containers and be ready for sale.

In some embodiments, as illustrated in FIGS. 2 and 3, the antenna 103 may be contained within the housing 206 and 220 of the transceiver 101. In some embodiments, the antenna 103 in the transceiver 101 may be small and/or flat so that the antenna 103 fits within the housing 206 and 220 of a small, lightweight transceiver 101. In some embodiments, the antenna 103 may be robust and capable of resisting various impacts. In some embodiments, the transceiver 101 may be suitable for placement, for example, on an abdomen area, upper-arm, wrist, or thigh of a patient body. In some non-limiting embodiments, the transceiver 101 may be suitable for attachment to a patient body by means of a biocompatible patch. Although, in some embodiments, the antenna 103 may be contained within the housing 206 and 220 of the transceiver 101, this is not required, and, in some alternative embodiments, a portion or all of the antenna 103 may be located external to the transceiver housing. For example, in some alternative embodiments, antenna 103 may wrap around a user's wrist, arm, leg, or waist such as, for example, the antenna described in U.S. Pat. No. 8,073,548, which is incorporated herein by reference in its entirety.

Figure 4:
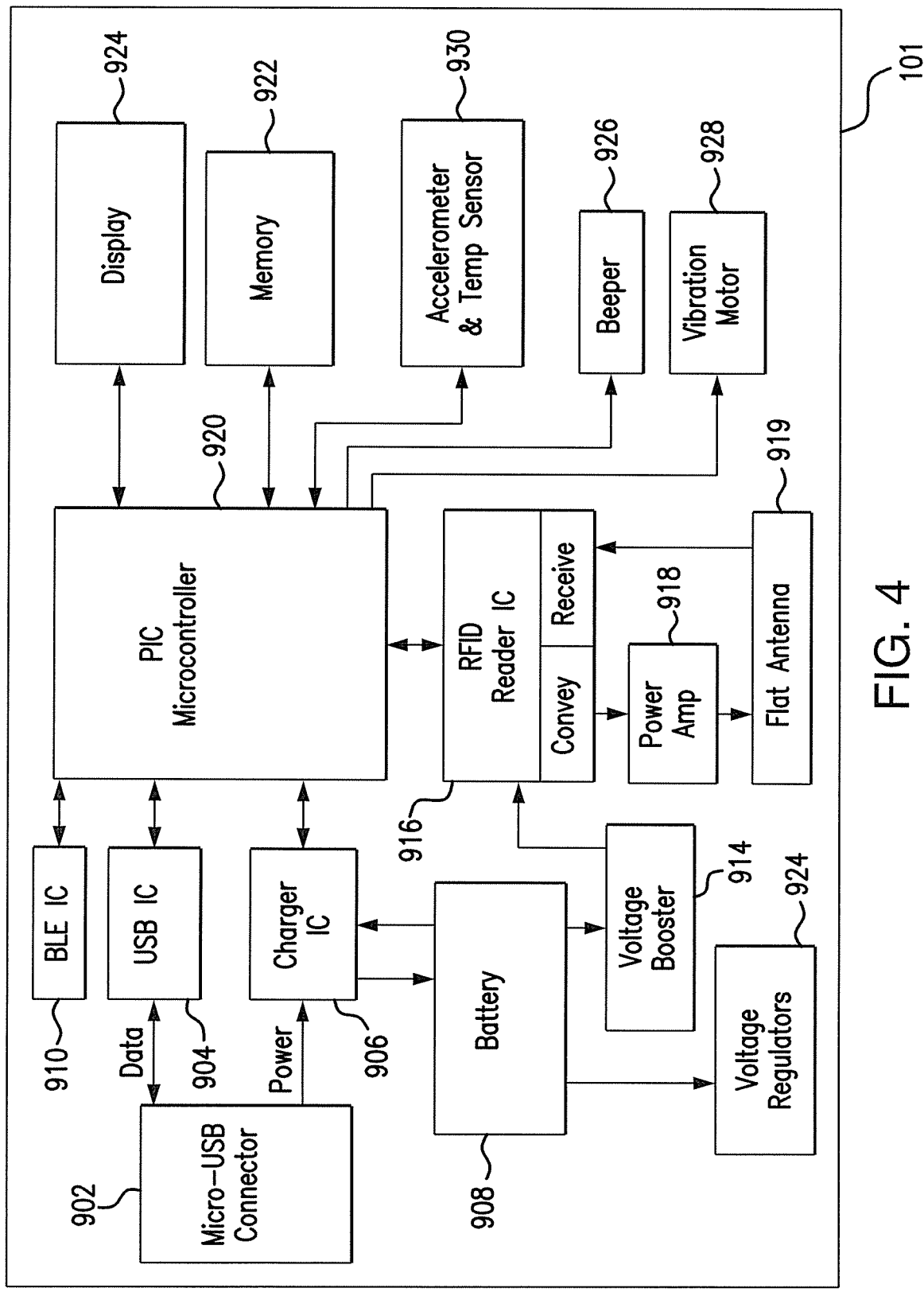
FIG. 4 is a schematic view illustrating a transceiver embodying aspects of the present invention.

FIG. 4 is a schematic view of an external transceiver 101 according to a non-limiting embodiment. In some embodiments, the transceiver 101 may have a connector 902, such as, for example, a Micro-Universal Serial Bus (USB) connector. The connector 902 may enable a wired connection to an external device, such as a personal computer (e.g., personal computer 109) or a display device 105 (e.g., a smartphone).

The transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge a battery 908 (e.g., lithium-polymer battery). In some embodiments, the battery 908 may be rechargeable, may have a short recharge duration, and/or may have a small size.

In some embodiments, the transceiver 101 may include one or more connectors in addition to (or as an alternative to) Micro-USB connector 904. For example, in one alternative embodiment, the transceiver 101 may include a spring-based connector (e.g., Pogo pin connector) in addition to (or as an alternative to) Micro-USB connector 904, and the transceiver 101 may use a connection established via the spring-based connector for wired communication to a personal computer (e.g., personal computer 109) or a display device 105 (e.g., a smartphone) and/or to receive power, which may be used, for example, to charge the battery 908.

In some embodiments, the transceiver 101 may have a wireless communication IC 910, which enables wireless communication with an external device, such as, for example, one or more personal computers (e.g., personal computer 109) or one or more display devices 105 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, the transceiver 101 may include a display interface device, which may enable communication by the transceiver 101 with one or more display devices 105. In some embodiments, the display interface device may include the antenna of the wireless communication IC 910 and/or the connector 902. In some non-limiting embodiments, the display interface device may additionally include the wireless communication IC 910 and/or the connector IC 904.

In some embodiments, the transceiver 101 may include voltage regulators 912 and/or a voltage booster 914. The battery 908 may supply power (via voltage booster 914) to radio-frequency identification (RFID) reader IC 916, which uses the inductive element 103 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 103 is a flat antenna. In some non-limiting embodiments, the antenna may be flexible. However, as noted above, the inductive element 103 of the transceiver 101 may be in any configuration that permits adequate field strength to be achieved when brought within adequate physical proximity to the inductive element 114 of the sensor 100. In some embodiments, the transceiver 101 may include a power amplifier 918 to amplify the signal to be conveyed by the inductive element 103 to the sensor 100.

The transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 103. The PIC microcontroller 920 may also control processing of data received via the inductive element 103, connector 902, or wireless communication IC 910.

In some embodiments, the transceiver 101 may include a sensor interface device, which may enable communication by the transceiver 101 with a sensor 100. In some embodiments, the sensor interface device may include the inductive element 103. In some non-limiting embodiments, the sensor interface device may additionally include the RFID reader IC 916 and/or the power amplifier 918. However, in some alternative embodiments where there exists a wired connection between the sensor 100 and the transceiver 101 (e.g., transcutaneous embodiments), the sensor interface device may include the wired connection.

In some embodiments, the transceiver 101 may include a display 924 (e.g., liquid crystal display and/or one or more light emitting diodes), which PIC microcontroller 920 may control to display data (e.g., glucose concentration values). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met. The transceiver 101 may also include one or more additional sensors 930, which may include an accelerometer and/or temperature sensor, that may be used in the processing performed by the PIC microcontroller 920.

Figure 5:
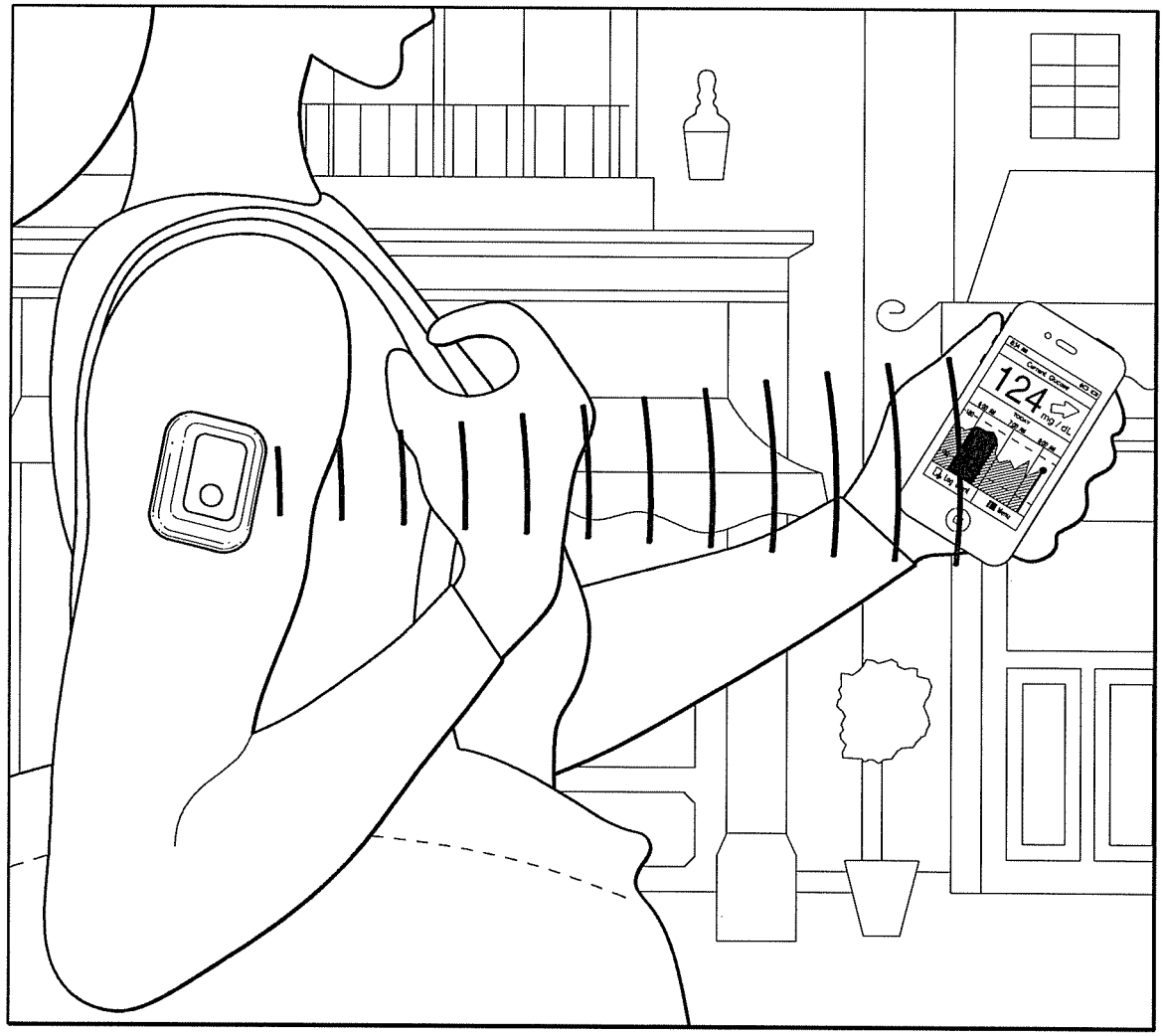
FIG. 5 illustrates a transceiver in wireless communication with a smartphone in accordance with an embodiment of the present invention.

In some embodiments, the transceiver 101 may be a body-worn transceiver that is a rechargeable, external device worn over the sensor implantation or insertion site. The transceiver 101 may supply power to the proximate sensor 100, calculate analyte concentrations from data received from the sensor 100, and/or transmit the calculated analyte concentrations to a display device 105 (see FIGS. 1A, 1B, and 5). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2 minutes) read sensor data and calculate an analyte concentration and an analyte concentration trend. From this information, the transceiver 101 may also determine if an alert and/or alarm condition exists, which may be signaled to the user (e.g., through vibration by vibration motor 928 and/or an LED of the transceiver's display 924 and/or a display of a display device 105). The information from the transceiver 101 (e.g., calculated analyte concentrations, calculated analyte concentration trends, alerts, alarms, and/or notifications) may be transmitted to a display device 105 (e.g., via Bluetooth Low Energy with Advanced Encryption Standard (AES)-Counter CBC-MAC (CCM) encryption) for display by a mobile medical application on the display device 105. In some non-limiting embodiments, the mobile medical application may provide alarms, alerts, and/or notifications in addition to any alerts, alarms, and/or notifications received from the transceiver 101. In one embodiment, the mobile medical application may be configured to provide push notifications. In some embodiments, the transceiver 101 may have a power button (e.g., button 208) to allow the user to turn the device on or off, reset the device, or check the remaining battery life. In some embodiments, the transceiver 101 may have a button, which may be the same button as a power button or an additional button, to suppress one or more user notification signals (e.g., vibration, visual, and/or audible) of the transceiver 101 generated by the transceiver 101 in response to detection of an alert or alarm condition.

In some embodiments, the transceiver 101 may provide on-body alerts to the user in a visual, audible, and/or vibratory manner, regardless of proximity to a display device 105. In some non-limiting embodiments, as illustrated in FIG. 4, the transceiver 101 may include one or more notification devices (e.g., display 924, beeper 926, and/or vibration motor 928) that generate visual, audible, and/or vibratory alerts. In some embodiments, the transceiver 100 may be configured to vibrate and/or generate an audio or visual signal to prompt the user about analyte readings outside an acceptable limit, such as hypo/hyper glycemic alerts and alarms in the case where the analyte is glucose.

In some embodiments, the vibrational, visual, and/or audible tone feedback provided by the transceiver 101 can enable the use of different patterns/rhythms/melodies that have various meanings corresponding to the status of the transceiver 101 and/or the implanted sensor 100 (e.g., for indicating the transceiver battery power level status and/or for locating the sensor 100 and determining the strength of connection between the sensor 100 and transceiver 101), or the analyte concentration. For example, in one non-limiting embodiment, the transceiver 101 might be calibrated to provide a long, repeatable vibration, with or without an audible/visual alarm, when a user's glucose concentration becomes too low or too high. In some embodiments, a vibration motor 928 of the transceiver 101 may communicate various messages/alerts to the user through Morse code like patterning and sequencing (e.g., long-long-short-short) and/or different vibration speeds and intensities. In a non-limiting embodiment, a circuit, such a supply voltage controller, may control the vibration speed and intensity. In some embodiments, different patterns of audio feedback, which may include different volumes, frequencies, time on-off (duty cycle), melodies, and/or rhythms may be used to communicate various messages/alerts to the user.

In some non-limiting embodiments, the transceiver 101 might be calibrated to provide a visual alert (e.g., one or more light emitting diodes (LEDs) of display 924 may turn on and off in a specific pattern and/or emit light of different intensities and/or frequencies/colors) when a user's glucose concentration becomes too low or too high. For example, in some non-limiting embodiments, the display 924 of the transceiver 101 may include dual LED (e.g., yellow/green) or a tri-color LED (i.e., blue/yellow/green). A display 924 providing different colors may enhance communication modes by adding color as variable. For instance, by using more than one LED (e.g., the dual LED or the tri-color LED) the display 924 may generate a blinking yellow-green-yellow-etc. visual signal and/or a long yellow-short yellow-short green-short green-etc. visual signal to communicate various messages/alerts to the user.

In a non-limiting embodiment, the combination of visual, audible, and/or vibratory patterns may communicate different messages/alerts than if the visual, audible, and/or visual, audible, and/or vibratory patterns were communicated alone. In some embodiments, the transceiver 101 may provide certain patterns of a vibratory and/or audible and/or visual alert to prompt the user when a calibration point is needed or is going to be needed, and/or when the battery needs to be recharged. In some embodiments, the display device 105 or other device communicating with the transceiver 101 may also have visual, audible, or vibratory alarms and notifications.

The vibrational, visual, and/or audible feedback of the transceiver 101 can also alert the user regarding the status of the telemetry system with the sensor 100. For example, for systems in which transceiver 101 delivers power to the implanted sensor 100 (e.g., by radio frequency signals via an inductive antenna), the visual, audible, and/or vibratory feedback can prompt the subject regarding how well the two systems are coupled. In other embodiments, the vibrational and/or audible feedback of the transceiver 101 can assist the user in adjusting the relative position of the transceiver 101 and optimize coupling between the transceiver 101 and the sensor 100 without having visual feedback. That is, the user can adjust the position of the transceiver 101 worn under a piece of clothing (e.g., shirt, etc.) without looking at the transceiver 101—the buzzer/vibrator signals of the transceiver 101 would indicate to the user if the sensor 100 is well within the range and if the readings are correct. Accordingly, in some embodiments, the transceiver 101 may be used to alert the user to optimal location of the transceiver 101 over the implanted sensor, which allows the user to adjust the transceiver 101.

Figure 6:
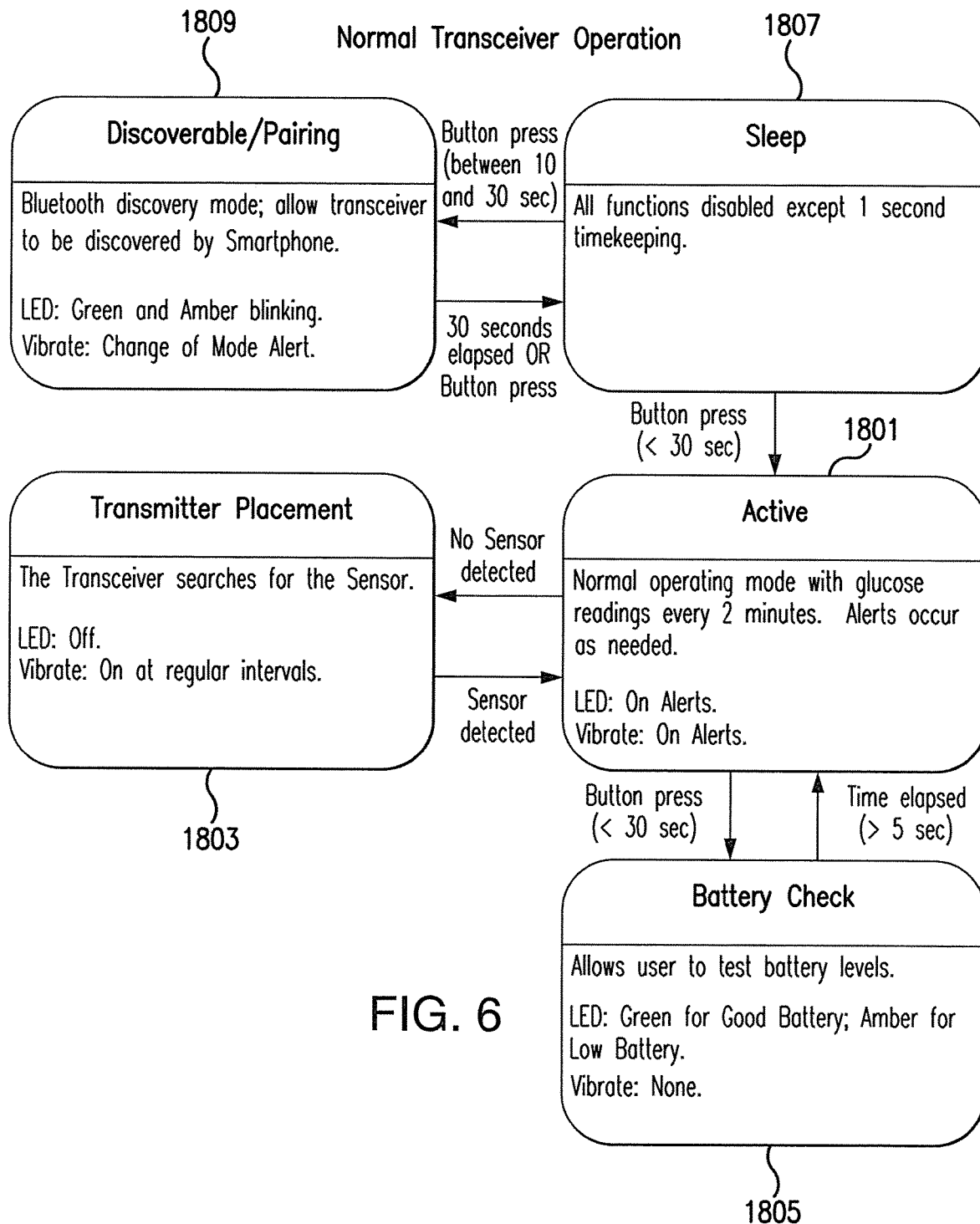
FIGS. 6 and 7 illustrate modes of operation for a transceiver embodying aspects of the present invention.

In some embodiments, as illustrated in FIG. 6, there may be several modes of operation for the transceiver 101. The transceiver 101 may include an active state 1801, which may be the normal state of the transceiver 101. In some non-limiting embodiments, the transceiver 101, when in the active state 1801, may be in direct communication with the sensor 100 and periodically power the sensor 100 and receive measurements therefrom.

As illustrated in FIG. 6, the transceiver 101 may include a transceiver placement state 1803. The transceiver 101 may enter the transceiver placement state 1803 from the active state 1801 if the transceiver 101 does not detect the sensor 100. When in the transceiver placement state 1803, the transceiver 101 may actively search for (i.e., attempt to locate) the sensor 100. In some non-limiting embodiments, the transceiver 101 may attempt to locate the sensor 100 by measuring the strength of magnetic coupling between the inductive elements 103 and 114 of the transceiver 101 and sensor 100 such as, for example, in the manner described in U.S. application Ser. No. 13/650,016, filed on Oct. 11, 2012, which is incorporated herein by reference in its entirety. The transceiver 101 may also include a battery check state 1805. The transceiver 101 may enter the battery check state 1805 from the active state 1801 if a button (e.g., button 208) on the transceiver 101 is pressed, and, when in the battery check state 1805, the display 924 of the transceiver 101 may show the remaining battery life of the transceiver 101.

In some embodiments, the transceiver 101 may include a sleep state 1807. In one non-limiting embodiment, the transceiver 101 may enter the sleep state 1807 from the active state 1801 if the transceiver button (e.g., button 208) is held for longer than a threshold period of time (e.g., 30 seconds). The transceiver 101 may include a discoverable/pairing state 1809. The transceiver 101 may enter the discoverable/pairing state 1809 from the sleep state 1807 if the transceiver is held for longer than a threshold period of time (e.g., 10 seconds). In the discoverable/pairing state 1809, the transceiver 101 may be paired with a display device 105 (e.g., a Bluetooth enabled smartphone).

Figure 7:
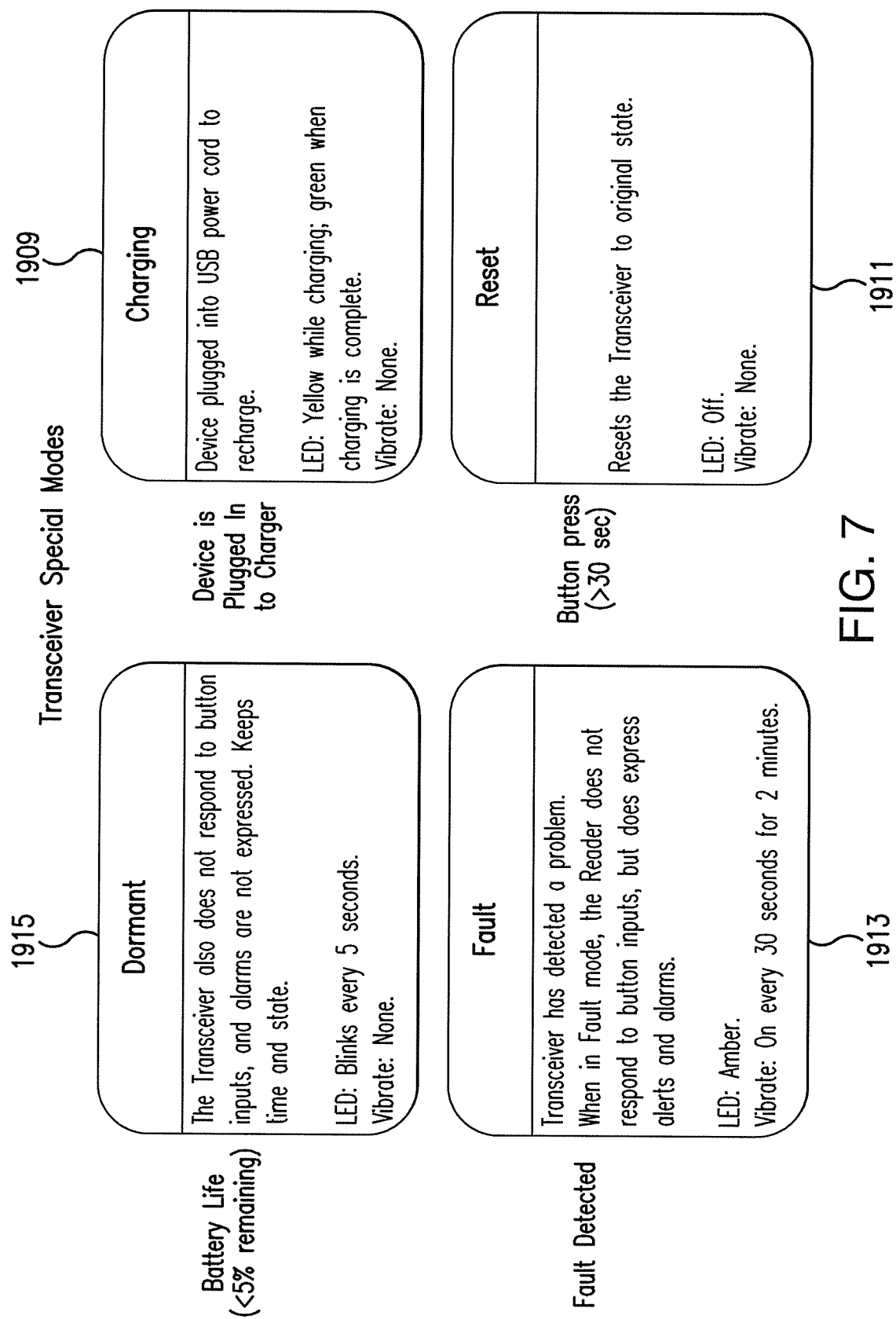

As illustrated in FIG. 7, the transceiver 101 may include a charging state 1909. The transceiver 101 may enter the charging state 1909 when the transceiver 101 is plugged into a charging system (e.g., via connector 902). While in the charging state 1909, the display 924 of the transceiver 101 may indicate that the transceiver 101 is charging (e.g., by an LED of the display 924 emitting yellow light) and/or may indicate that charging is complete (e.g., by an LED of the display 924 emitting green light).

As illustrated in FIG. 7, the transceiver 101 may include a reset state 1911. The transceiver 101 may enter the reset state 1911 in response to a user input (e.g., holding a transceiver button for more than a predetermined amount of time, such as, for example, 30 seconds). While in the reset state 1911, the transceiver 101 may return to its original settings.

As illustrated in FIG. 7, the transceiver 101 may include a fault state 1913. The transceiver 101 may enter the fault state 1913 if the transceiver 101 detects an internal problem. While in the fault state 1913, the transceiver 101 may alert the user that the transceiver 101 is not working properly (e.g., by an LED of display 924 emitting amber or red light).

As illustrated in FIG. 7, the transceiver 101 may include a dormant state 1915. The transceiver 101 may enter the dormant state 1913 if the transceiver 101 detects that the battery life of battery 908 falls below a threshold (e.g., 5% of capacity). While in the dormant state 1915, the transceiver 101 may alert the user that battery life is low and that the battery should be recharged.

In some embodiments, the transceiver 101 may pass between states (e.g., the states described above with reference to FIGS. 6 and 7) under the control of the microcontroller 920. In other words, the microcontroller 920 may be configured to control the transceiver 101 in the transceiver states and to pass from one state to another.

In some embodiments, the transceiver 101 may store the measurement information received from the sensor 100 (e.g., in memory 922). As noted above, the measurement information received from the sensor 100 may include one or more of: (i) a signal channel measurement with light source 108 on, (ii) a reference or second signal channel measurement with light source 108 on, (iii) a light source current source voltage measurement, (iv) field current measurement, (v) a diagnostic measurement, (vi) an ambient signal channel measurement with light source 108 off, (vii) an ambient reference or second signal channel measurement with light source 108 off, and (viii) a temperature measurement. In some embodiments, the transceiver 101 may additionally store (e.g., in memory 922) other data with the measurement information received from the sensor 100. In some non-limiting embodiments, the other data may include one or more of: (i) an analyte concentration (e.g., in mg/dL, such as, for example, within a range of 20.0 to 400.0 mg/dL) calculated by the transceiver 101 from the measurement information, (ii) the date and time that the analyte measurement was taken, (iii) accelerometer values (e.g., x, y, and z) taken from an accelerometer of the transceiver 101 (e.g., an accelerometer of additional sensors 930), and/or (iv) the temperature of the transceiver 101 as measured by a temperature sensor of the transceiver 101 (e.g., a temperature sensor of additional sensors 930). In some embodiments, the transceiver 101 may keep track of the date and time and, as noted above, store the date and time along with the received analyte measurement information and/or calculated analyte concentration. In embodiments where the transceiver 101 includes an accelerometer, the accelerometer will enable tracking of activity levels of the subject that is wearing the transceiver 101. This activity level may be included in an event log and incorporated into various algorithms (e.g., for analyte concentration calculation, trending, and/or contributing to potential dosing levels for the subjects). In some embodiments, the transceiver 101 may store (e.g., in memory 922) any alert and/or alarm conditions detected based on the calculated analyte concentrations.

In some embodiments, the transceiver 100 may include a Global Positioning System (GPS) unit having the functionality to acquire a GPS signal. The GPS unit may implement hardware and/or software functionality that enables monitoring of motion. In some non-limiting embodiments, the GPS unit may improve glucose monitoring by providing motion information that can be used to help determine movement-related artifacts or noise that may be present within the monitoring signal. In some embodiments, the transceiver 100 may additionally or alternatively use information from the GPS unit to provide feedback to the user of the sensor system in order to aid the user in, for example, moving the sensor 324 to the correct position or orientation. In some embodiments, the GPS unit may provide the transceiver 100 with the ability to communicate exact positions for patients that may go into hypoglycemic shock and would need emergency personal notified of their location for treatment. For example, the location of the patient may be communicated through the transceiver's wireless capabilities and/or through a cellular or wifi handset.

In some embodiments, the mobile medical application executing on the display device 105 may be configured to send text messages and/or emails to other devices (e.g., at telephone numbers and/or email addresses of family members, guardians, emergency contacts, doctors, medical staff, etc.) with information regarding analyte status (e.g., analyte concentrations, trends, alerts, alarms, notifications).

In some embodiments, the transceiver 101, sensor 100, or mobile medical application executing on a display device 105 may initiate a call (e.g., via a display device 105 that is a smartphone) to appropriate emergency number in case of an emergency. In one embodiment, a wearable external transceiver 101 or a user interface displayed by the mobile medical application executing on a display device 105 may include an emergency button that will initiate a call with the emergency number for the live location of the patient. In this embodiment, the patient may enter emergency contact information through a software program. For example, in a non-limiting embodiment, the patient's doctor will have access to the software and input the emergency contact information during a doctor's visit, and/or the patient will have access to a web interface where the patient can login and enter the emergency contact information themselves. The emergency contact information may be stored on an external device (e.g., a remote server) or as data in the external transceiver 101, implanted sensor 100, or display device 105. In one non-limiting embodiment, in case of an emergency, pressing the emergency button on the transceiver 101 and/or analyte levels reaching dangerous levels for an extended period of time may cause the transceiver 101 to automatically transmit a signal to a display device 105 or other device that will call a programmed caregiver or hospital depending on the patient's location.

In one non-limiting embodiment, transceiver 101 will send a signal to call the programmed emergency contact if it senses low (or high) analyte and idle movement for an extended period of time (e.g., latitude/longitude not changing in GPS tracker) along a roadway, river, etc. The transceiver 101 or sensor 100 may include a timer pre-programmed to a specific length of time and may generate an initial "no movement detected/low analyte" alert that will sound a cell phone (e.g., a display device 105 that is a smartphone) or other similar device before initiating an emergency contact. The patient may be able to silence the alert if they are not moving on purpose (e.g., sitting in a movie, concert, or long car ride), but, because the alert also indicates a low (or high) analyte concentration, the patient will be able to alleviate the issue and raise (or lower) their analyte level before the levels drop too low (or go too high). In some embodiments, transceiver 101 may alert a cell phone (e.g., a display device 105 that is a smartphone) or other device when an analyte concentration is low or high and indicate where the nearest market, clinic, and/or pharmacy is based upon the patient's location.

In some embodiments where the transceiver 101 has a GPS unit, the transceiver may adjust analyte concentration calculations based on the altitude of the patient. In doing so, the analyte monitoring system may ensure that analyte readings remain accurate even with changing altitude.

In some embodiments, the transceiver 100 may include splash-proof/water resistant or waterproof features. This would enable the user to use the transceiver 100 according to appropriate guidelines of those standards. For example, in embodiments where the transceiver 100 is waterproof, a user could take as shower while wearing the waterproof transceiver 100.

Figure 8:
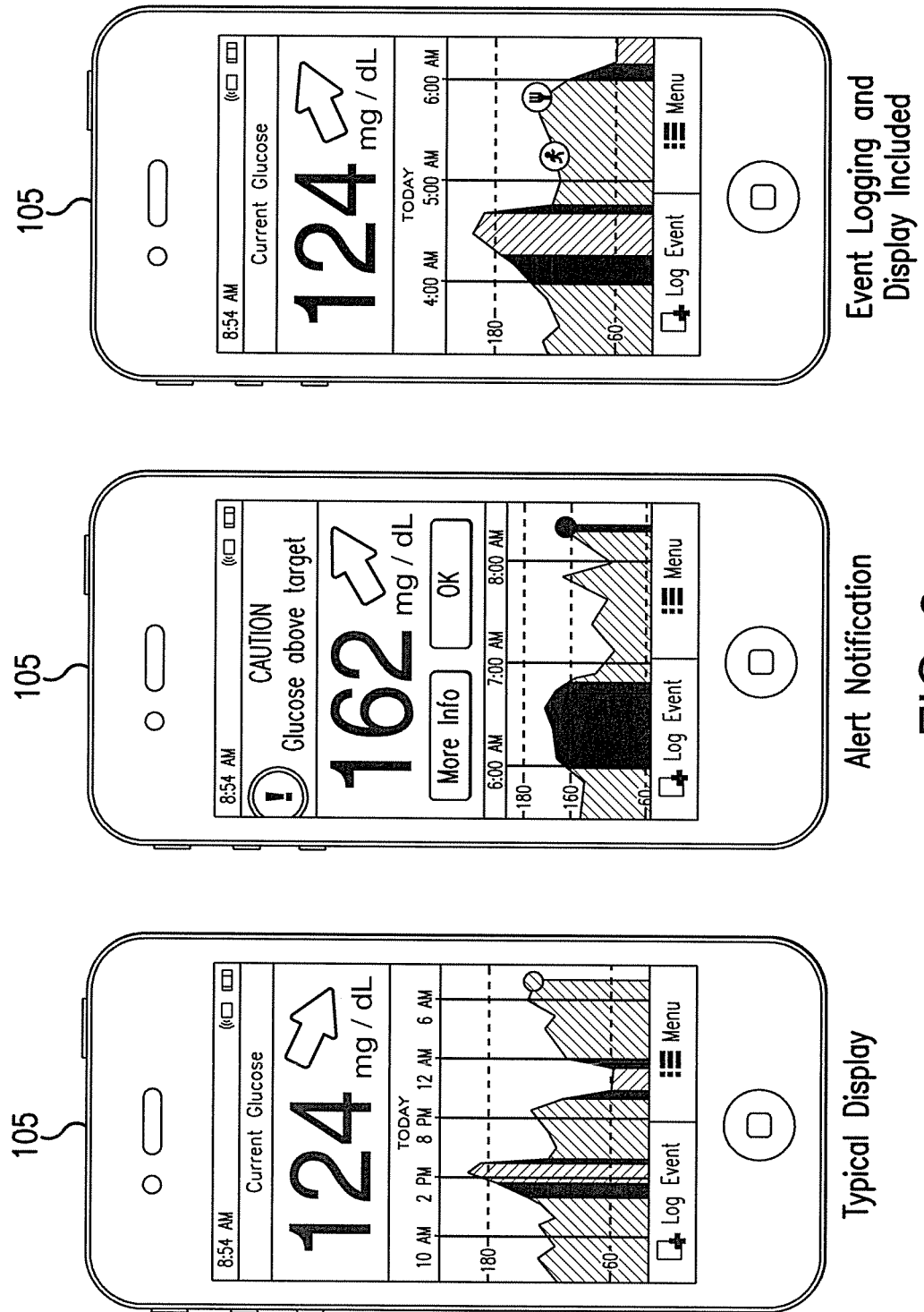
FIG. 8 illustrates a mobile medical application display on a smartphone embodying aspects of the present invention.

In some embodiments, as illustrated in FIG. 8, the display device 105 may have a mobile medical application installed thereon that, when executed by the display device 105, displays analyte values (e.g., "124 mg/dL"), trends (e.g., upward or downward), graphs, alerts (e.g., "glucose above target"), and/or alarms (e.g., indicating that a hyperglycemic or hypoglycemic condition has been reached). In some embodiments, the transceiver 101 may calculate the analyte concentrations and trends and detect the alert and/or alarm conditions and push the concentrations, trends, alerts, and/or alarms to the display device 105 for display. In this way, transceiver 101 may update data displayed by the display device 105 (i.e., the data displayed by the display device 105 may be synchronized with the data calculated by the transceiver 101), and the display device 105 may mirror data calculated by and received the transceiver 101 by displaying it to the user. In some embodiments, the display device 105 does not perform its own calculations, but this is not required, and, in some alternative embodiments, the medical application executed on a display device 105 may calculate analyte concentrations and/or trends and/or detect alert and/or alarm conditions based on data received from the transceiver 101. In some embodiments, the transceiver 101 may not display the calculated concentrations and/or trends itself. However, this is not required, and, in some alternative embodiments, the transceiver 101 and one or more display devices 105 may redundantly display the calculated concentrations and/or trends. In one non-limiting embodiment, the transceiver 101 (i) calculates but does not display analyte concentrations and trends, (ii) detects alert and alarm conditions and notifies the user of detected alert and alarm conditions (e.g., via vibration, audible, and/or visual feedback), and (iii) pushes the calculated analyte concentrations and trends and the detected alerts and alarms to a display device 105 for display by the medical application. In some embodiments, the mobile medical application allows the user to set predetermined alarm and alert thresholds.

In some embodiments, transceiver 101 (or the display device 105 in some alternative embodiments) calculate an analyte concentration trend by estimating the slope between the analyte concentration calculated from the previous sensor reading and the analyte concentration calculated from the current sensor reading. In some embodiments, the trend may be recalculated at every sensor reading. A user may use the trend to know how to respond to their analyte level more effectively in order to keep it in a healthy range. In some non-limiting embodiments where the analyte is glucose, the glucose trend/rate between two data points may be calculated as follows:

$$\text{Rate} = (G_{New} - G_{Old})/(T_{Old} - T_{New}) \qquad (1)$$

where: $G_{New}$=average of three most recent glucose measurements, $G_{Old}$=average of next three most recent glucose measurements, $T_{New}$=average time at which three most recent glucose measurements were taken, and $T_{Old}$=average time at which next three most recent glucose measurement were taken. However, this is not required, and, in alternative embodiments, the transceiver 101 may calculate the trend in different ways.

In some embodiments where the analyte is glucose and the system includes the display device 105, a user may have the option of using a mobile medical application executed by the display device 105 to set target, alert, and/or alarm levels for hypoglycemia and hyperglycemia so that the user's glucose levels stay within the eugylcemia range, which is between about 75 and 165 mg/dL for a normal person. In some non-limiting embodiments, the user may set an alert level, and, when the calculated glucose concentration reaches a level that is too low (hypoglycemia) or a level that is too high (hyperglycemia), the smartphone may warn/alert the user (e.g., by beeping briefly, vibrating briefly, and/or displaying an alert message on a background having a first color, such as yellow). In some non-limiting embodiments, a user may set an alarm level, which is a level at which the value of glucose is significantly too high or low, and, when the calculated glucose concentration reaches an alarm level, the display device 105 may warn the user using an alarm (e.g., a longer beep, a longer vibration, and/or an alarm message on a background having a second color, such as red) that is distinguishable from the alert indicating that the alert level has been reached.

Figure 9:
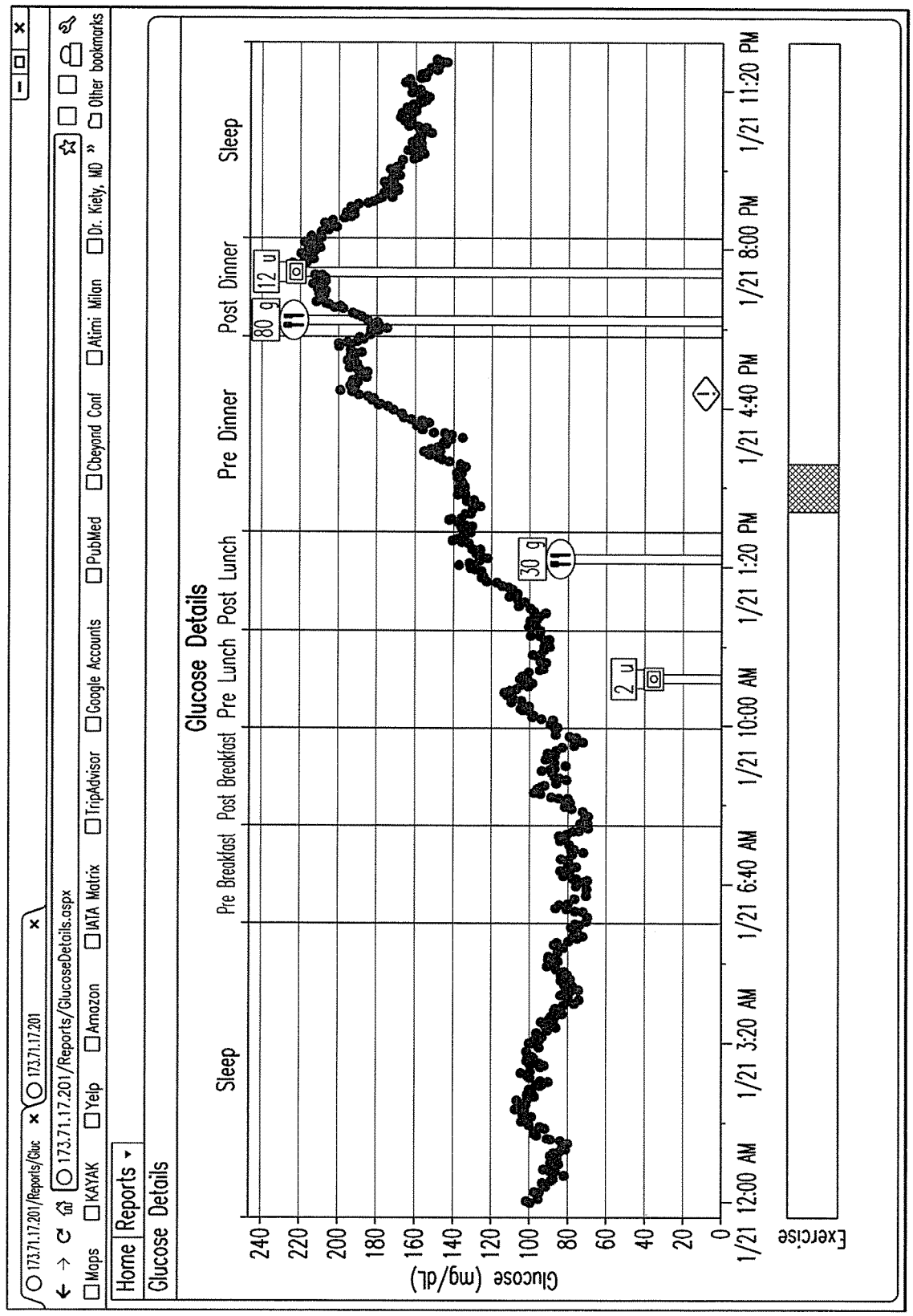
FIG. 9 illustrates an analyte details report generated by a data management system of an analyte monitoring system embodying aspects of the present invention.
Figure 10:
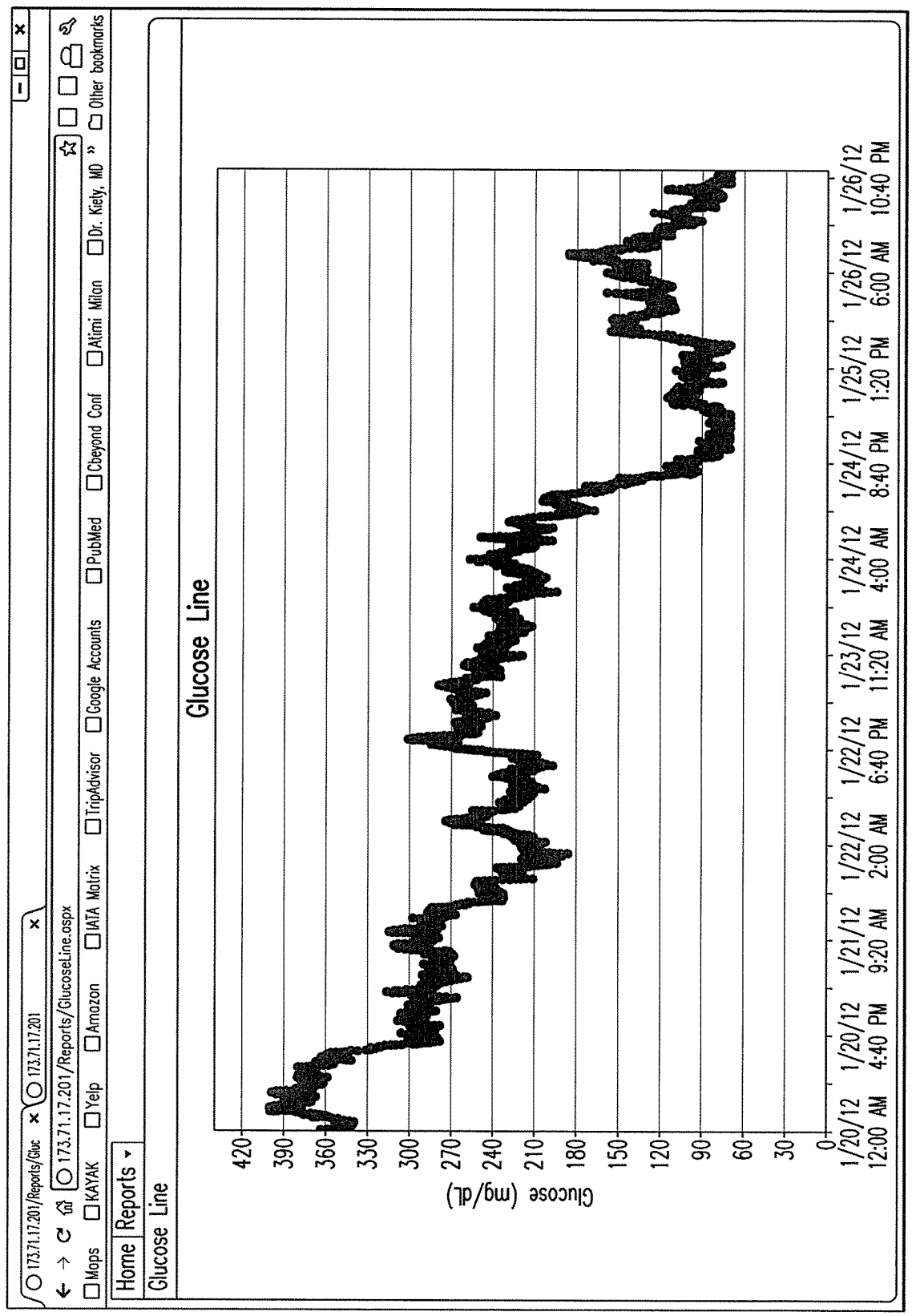
FIG. 10 illustrates an analyte line report generated by a data management system of an analyte monitoring system embodying aspects of the present invention.
Figure 11:
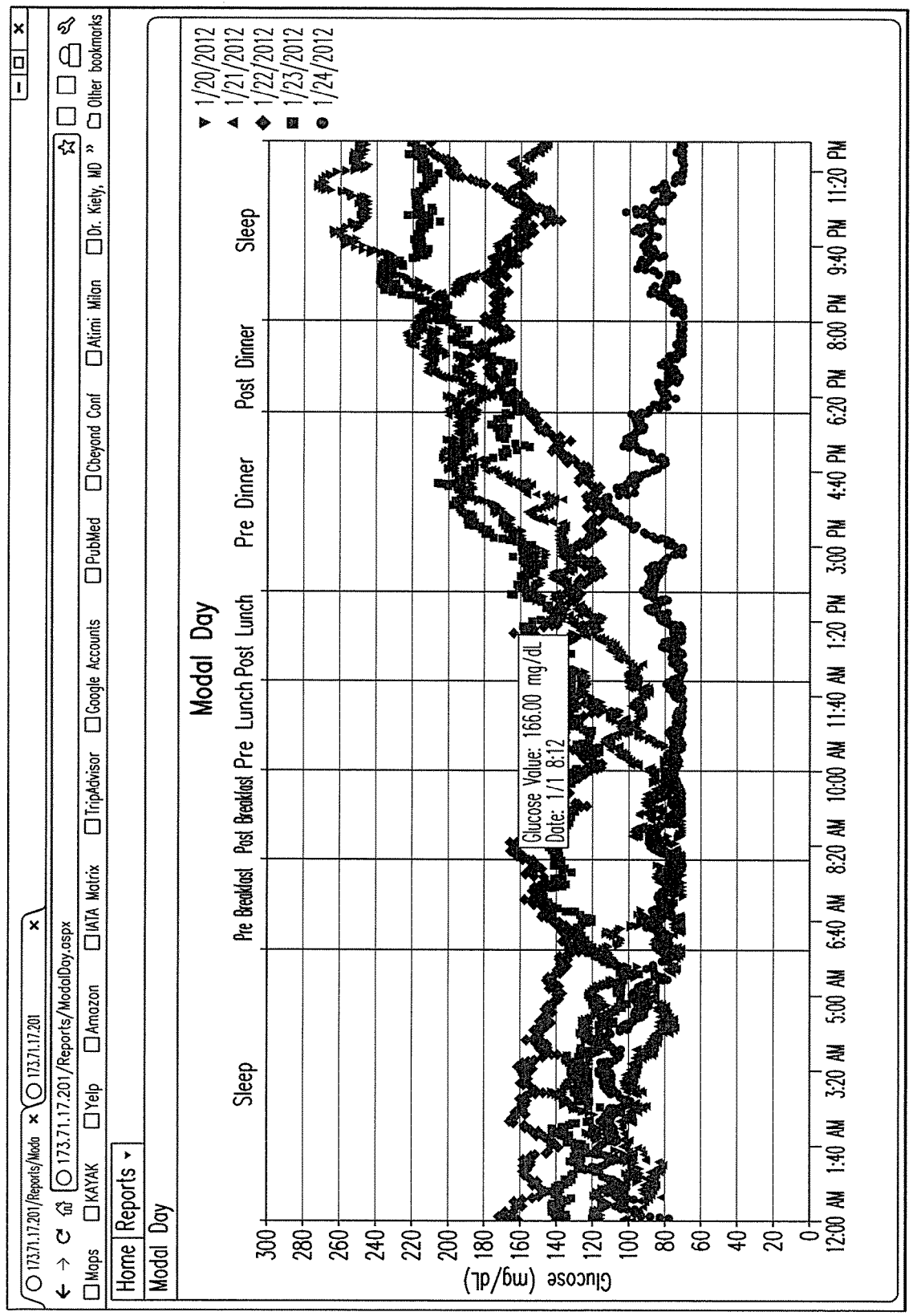
FIG. 11 illustrates a modal day report generated by a data management system of an analyte monitoring system embodying aspects of the present invention.
Figure 12:
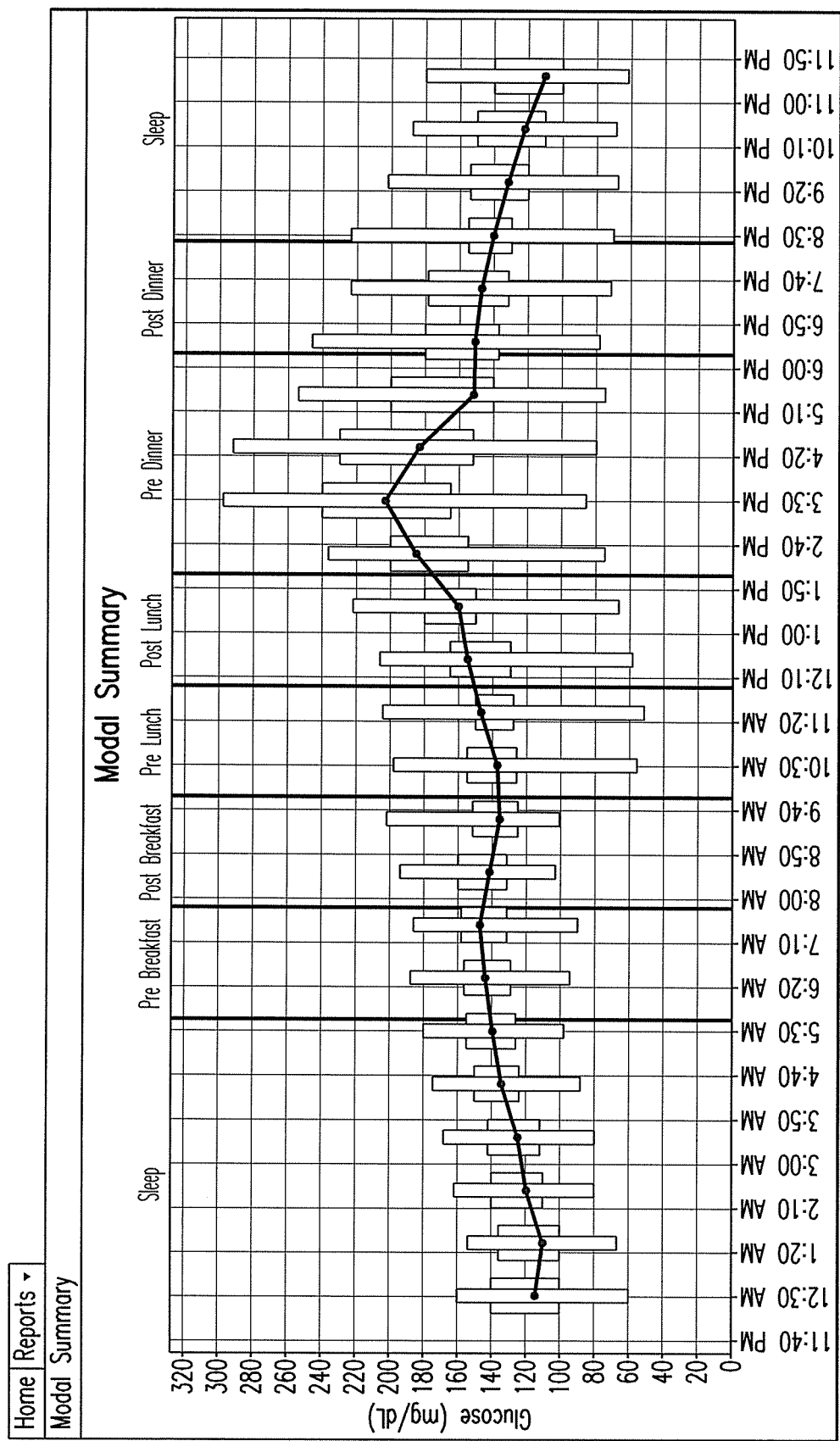
FIG. 12 illustrates a modal summary report generated by a data management system of an analyte monitoring system embodying aspects of the present invention.
Figure 13:
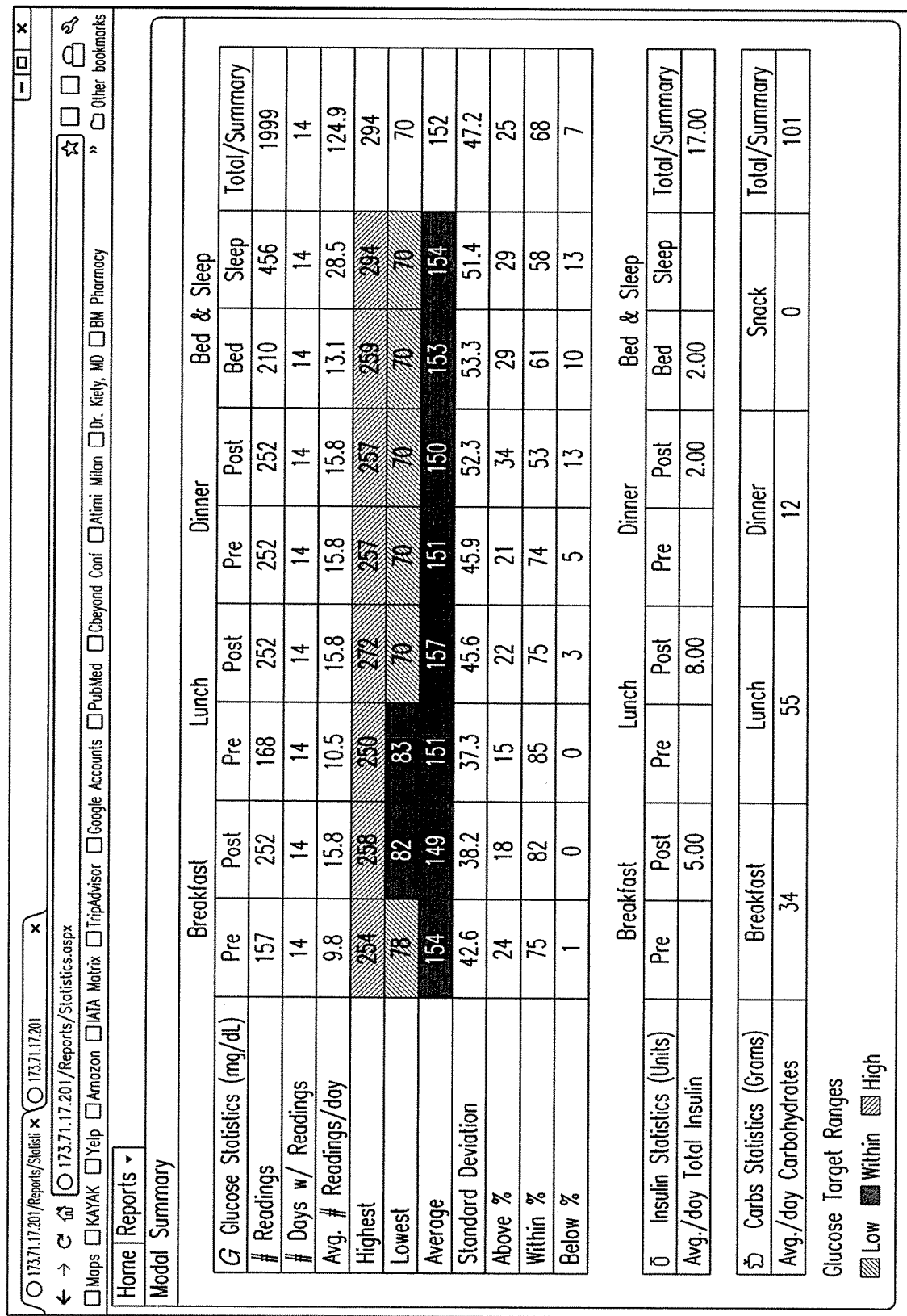
FIG. 13 illustrates a statistics report generated by a data management system of an analyte monitoring system embodying aspects of the present invention.

In some embodiments, the mobile medical application executed by the display device 105 may be configured to accept user-entered physiological events, log the events, and display the events. In some non-limiting embodiments, the physiological events may include, for example, insulin, meal/carb, exercise, and/or health/illness events. In some embodiments, the mobile medical application may display the events on a graph plotting the calculated analyte concentrations. FIG. 9 includes an example of a display device 105 displaying a logged exercise event and a logged meal event on a graph plotting analyte concentrations.

In some embodiments where the system includes the data management system (DMS) 111 (see FIG. 1B), the DMS 111 may be a web-based analyte DMS. In some embodiments, data from the display device 105 and/or PC 109 may be uploaded (e.g., through a wired connection such as, for example, a USB connection or a wireless connection such as, for example, a wireless Internet connection) to a web server on a remote computer. In some embodiments, the DMS 111 may enable sharing of the analyte data (e.g., allowing the user, caregiver, and/or clinician to view sensor analyte data). The user may collect analyte data at home or in a clinic/research facility and then upload the data to their computer web account. Using the web account, the DMS 111 may use the data to generate one or more different reports utilizing the uploaded information. For example, in some non-limiting embodiments, the DMS 111 may use the uploaded data to generate one or more of the following reports: (i) an analyte details report, (ii) an analyte line report, (iii) a modal day report, (iv) a modal summary report, (v) a statistics report, and (vi) a transceiver log report. Examples of the different reports that may be generated by the DMS 111 are illustrated in FIGS. 9-14, respectively.

In some embodiments, a user may use the DMS 111 to register with the DMS 111 and create a unique user ID and password. Once logged in, the user may enter their basic user information and may upload analyte reading data from their transceiver 101. In various embodiments, the DMS 111 may support specific data types such as, for example, glucose, insulin, meal/carbs, exercise, health event, alarms, and errors. In some non-limiting embodiments, data can be automatically uploaded or entered manually by the user or imported from the transceiver 101 and then saved in the DMS 111 to be viewed at a later date.

In some embodiments, the each sensor 100 and/or each transceiver 101 may include traceability information, such as, for example, a unique identifier. In some embodiments, a transceiver 101 may receive a unique identifier from a sensor 100 and decode the unique identifier. Based on the decoded unique identifier, the transceiver 101 may identify the sensor's manufacturing information, which may be useful in purifying analyte measurements received from the sensor 100 and/or calculating analyte concentration. For example, in some non-limiting embodiments, the transceiver 101 may use manufacturing information to purify received analyte measurements and/or calculate analyte concentrations in the manner described in U.S. application Ser. No. 13/937,871, filed on Jul. 9, 2013, which is incorporated herein by reference in its entirety. In some non-limiting embodiments, the transceiver 101 may be capable of calculating analyte concentrations in units of mg/dL and/or mmol.

In some embodiments, the sensor 100 may receive a unique identifier of a transceiver 101 and use the transceiver's unique identifier to determine whether the transceiver 101 is a different transceiver 101 than the transceiver 101 last used with the sensor 100 and/or whether the transceiver 101 has not been previously used with the sensor 100. The sensor 100 may use this information to determine whether to convey any previous analyte measurement information stored on the sensor 100 to the transceiver 101 to update/fill in any gaps in the transceiver's records. Additionally or alternatively, in some embodiments, a display device 105 and/or web-based DMS 111 may use a unique identifier of a transceiver 101 to determine whether to convey information such as, for example, calibration information and/or user preferences to the transceiver 101.

In some embodiments, the transceiver 101 may perform a calibration regimen. In some non-limiting embodiments, the transceiver 101 may calibrate itself using analyte measurements received from the sensor 100 and one or more analyte calibration measurements (e.g., finger-stick self-monitoring blood glucose (SMBG) measurements). In some non-limiting embodiments, the user may wait until after the sensor 100 has been implanted for 24 hours to calibrate the sensor 100. In some non-limiting embodiments, the user may calibrate the sensor 100 using four finger stick measurements each separated by at least two hours. After an initial calibration, the system may request one or more additional finger stick measurements to recalibrate the sensor 100. For example, in one non-limiting embodiment, after the initial calibration, the system may request two finger stick measurements (i.e., calibration data points) each day, and the finger stick measurements may be separated by 10-14 hours. In some non-limiting embodiments, a user may enter analyte calibration measurements using the medical application executed by the display device 105 and/or the DMS 111, and the transceiver 101 may download the entered analyte calibration measurements from the display device 105 and/or the DMS 111.

For instance, in one particular non-limiting embodiment where the analyte is glucose, the calibration regimen may involve three phases: (i) a warm-up phase during the first 24 hours after implantation in which glucose levels are not calculated, (ii) an initialization phase starting at 24 hours after implantation and ending after acquiring four finger-stick SMBG calibration points separated by a minimum of 2 hours, and (iii) a daily calibration phase starting after the last calibration of the initialization phase. In some embodiments, the user may set the daily calibration times (e.g., 8 am and 6 pm). In some non-limiting embodiments, analyte calibration measurements may be limited to calibration points falling within specified ranges (e.g., glucose readings greater than 60 mg/dL and less than 300 mg/dL during rates of glucose change less than 2.5 mg/dL/min). In some embodiments, the user may enter the calibration points of the initialization phase and/or daily calibration phase into the analyte monitoring system via a user interface of the transceiver 101 or display device 105. In non-limiting embodiments where the user enters the calibration points via the user interface of the display device 105, the display device 105 may convey the entered calibration points to the transceiver via wired or wireless communication.

In some embodiments, the analyte monitoring system may include an insulin pump, and the transceiver 101 and/or a display device 105 may convey analyte concentrations and/or insulin delivery commands to an insulin pump controller, which may adjust the insulin output of the insulin pump as part of a closed-loop insulin delivery system (i.e., artificial pancreas).

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

For example, although embodiments have been described in which the transceiver 101 (e.g., the microcontroller 920 of transceiver 101) calculates analyte concentrations based on the measurement information, this is not required. In some alternative embodiments, the transceiver 101 may instead covey/relay the measurement information received from the sensor 100 to another device for calculation of analyte concentrations without performing analyte concentration calculations. In some non-limiting alternative embodiments, the transceiver 101 may relay analyte measurement information received from the sensor 100 to the display device 105. A mobile medication application executing on the display device 105 may calculate analyte concentrations based on the measurement information received from the transceiver 101. In some non-limiting alternative embodiments, the display device 105 may purify received analyte measurement information and/or calculate analyte concentrations in the manner described in U.S. application Ser. No. 13/937,871, filed on Jul. 9, 2013, which is incorporated herein by reference in its entirety. Also, in some non-limiting embodiments, the display device 105 may calculate analyte concentration trends (regardless of whether calculation of the analyte concentrations is performed by the transceiver 101 or the display device 105).

What is claimed is:

1. A system for detecting an amount or concentration of an analyte in vivo within a living organism, the system comprising:
   an analyte sensor comprising:
      an analyte indicator configured to exhibit a detectable property based on the amount or concentration of the analyte in proximity to the analyte indicator;
      sensor elements including a temperature sensor, wherein the sensor elements are configured to generate sensor measurements including one or more measurements based on the detectable property exhibited by the analyte indicator and one or more measurements based on an output of the temperature sensor; and a transceiver interface device that comprises an antenna and is configured to wirelessly convey the sensor measurements generated by the sensor elements; a transceiver comprising a sensor interface device that includes an antenna and is configured to receive the sensor measurements conveyed by the transceiver interface device of the analyte sensor, wherein the transceiver is configured to:
communicate with the analyte sensor using a first wireless communication standard and receive the sensor measurements from the analyte sensor; and employ a second wireless communication standard to convey the sensor measurements, wherein the first and second wireless communication standards are different; and
a display device configured to:
receive the sensor measurements from the transceiver;
calculate an analyte concentration using at least the received sensor measurements; display the calculated analyte concentration receive one or more user-entered calibration points; and
perform an analyte concentration calibration based on at least the one or more user-entered calibration points.

2. The system of claim 1, wherein the first wireless communication standard is a near field communication (NFC) standard.

3. The system of claim 1, wherein the second wireless communication standard is a Bluetooth or Bluetooth Low Energy standard.

4. The system of claim 3, wherein the first wireless communication standard is a near field communication (NFC) standard.

5. The system of claim 1, wherein the analyte is glucose.

6. The system of claim 1, wherein the analyte sensor is an implantable sensor.

7. The system of claim 1, wherein the display device is configured to calculate an analyte concentration trend using at least the calculated analyte concentration.

8. The system of claim 7, wherein the display device is configured to generate one or more alerts or alarms based on one or more of the calculated analyte concentration and the calculated analyte concentration trend.

9. The system of claim 1, wherein the display device is a smartphone.

10. A method for detecting an amount or concentration of an analyte in vivo within a living organism, the method comprising:
using an antenna of a sensor interface device of a transceiver to communicate with an analyte sensor using a first wireless communication standard and wirelessly receive sensor measurements from an antenna of a transceiver interface device of the analyte sensor, wherein the sensor measurements include one or more measurements based on a detectable property exhibited by an analyte indicator of the analyte sensor and one or more measurements based on an output of a temperature sensor of the analyte sensor;
using the transceiver to employ a second wireless communication standard to convey the sensor measurements, wherein the first and second wireless communication standards are different; and
using a display device to receive the sensor measurements from the transceiver;
using the display device to calculate an analyte concentration using at least the received sensor measurements;
using the display device to display the calculated analyte concentration;
using the display device to receive one or more user-entered calibration points; and
using the display device to perform an analyte concentration calibration based on at least the one or more user-entered calibration points.

11. The method of claim 10, wherein the first wireless communication standard is a near field communication (NFC) standard.

12. The method of claim 10, wherein the second wireless communication standard is a Bluetooth or Bluetooth Low Energy standard.

13. The method of claim 12, wherein the first wireless communication standard is a near field communication (NFC) standard.

* * * * *